US009492418B2

(12) United States Patent
Lee et al.

(10) Patent No.: US 9,492,418 B2
(45) Date of Patent: Nov. 15, 2016

(54) INHIBITORS OF PFKFB3 FOR CANCER THERAPY

(75) Inventors: Yong-Hwan Lee, Baton Rouge, LA (US); Jeong Do Kim, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/467,764

(22) Filed: May 9, 2012

(65) Prior Publication Data

US 2012/0302631 A1 Nov. 29, 2012

Related U.S. Application Data

(60) Provisional application No. 61/484,386, filed on May 10, 2011.

(51) Int. Cl.
| | | |
|---|---|---|
| *A61K 31/37* | (2006.01) | |
| *A61K 31/222* | (2006.01) | |
| *A61P 3/00* | (2006.01) | |
| *A61K 31/352* | (2006.01) | |

(52) U.S. Cl.
CPC .......... *A61K 31/222* (2013.01); *A61K 31/352* (2013.01); *A61K 31/37* (2013.01)

(58) Field of Classification Search
None
See application file for complete search history.

(56) References Cited

U.S. PATENT DOCUMENTS

2009/0074884 A1   3/2009   Chesney et al. .............. 424/649

FOREIGN PATENT DOCUMENTS

WO    WO 2012116151 A2 *  8/2012

OTHER PUBLICATIONS

Atsumi, High Expression of Inducible 6-Phosphofructo-2-Kinase/Fructose-2,6-Bisphosphatase (iPFK-2 PFKFB3) in Human Cancers, Cancer Research, 2002, 62, pp. 5881-5887.*
Atsumi, T., et al., High expression of inducible 6-phosphofructo-2-kinase/fructose-2,6-bisphosphatase (iPFK-2; PFKFB3) in human cancers, Cancer Research, vol. 62, pp. 5881-5887 (2002).
Beene, D.L. et aL, "Cation-pi interactions in ligand recognition by serotonergic (5-HT3A) and nicotinic acetylcholine receptors: the anomalous binding properties of nicotine," Biochemistry, vol. 41, pp. 10262-10269 (2002).
Blundell, T.L. et al., "High-throughput crystallography for lead discovery in drug design," Nat Rev Drug Discov, vol. 1 pp. 45-54 (2002).
Calvo M.N. et al., "PFKFB3 gene silencing decreases glycolysis, induces cell-cycle delay and inhibits anchorage-independent growth in HeLa cells," FEBS Lett , vol. 580, pp. 3308-3314 (2006).

(Continued)

*Primary Examiner* — San-Ming Hui
*Assistant Examiner* — Andrew Lee
(74) *Attorney, Agent, or Firm* — John H. Runnels; Bonnie J. Davis

(57) ABSTRACT

Compounds used to inhibit glycolytic pathway small molecule kinase 6-Phosphofructo-2-kinase/Fructose-2,6-bisphosphatase (PFKFB) are set forth; these inhibitors can be used in the treatment of certain diseases in which cells or tumors rely on glycolytic metabolism, such as many cancer cells.

5 Claims, 15 Drawing Sheets

(56) References Cited

OTHER PUBLICATIONS

Chesney, J., "6-phosphofructo-2-kinase/fructose-2,6-bisphosphatase and tumor cell glycolysis," Curr. Opin. Clin. Nutr. Metab. Care., vol. 9, No. 5, pp. 535-539 (2006).
Cleland, W.W., "Statistical analysis of enzyme kinetic data," Methods Enzymol, vol. 63, pp. 103-138 (1979).
Clem, B. et al., "Small-molecule inhibition of 6-phosphofructo-2-kinase activity suppresses glycolytic flux and tumor growth," Mol Cancer Ther, vol. 7, pp. 110-120 (2008).
Davies, S.P. et al., "Specificity and mechanism of action of some commonly used protein kinase inhibitors," Biochem J, vol. 351, pp. 95-105 (2000).
DeBerardinis, Ralph J. et al., "The biology of cancer: metabolic reprogramming fuels cell growth and proliferation," Cell Metab, vol. 7, pp. 11-20 (2008).
El-Maghrabi, M.R. et al., "6-phosphofructo-2-kinase/fructose-2,6-bisphosphatase: suiting structure to need, in a family of tissue-specific enzymes," Curr Opin Clin Nutr Metab Care, vol. 4, pp. 411-418 (2001).
Ewing, Todd J.A. et al., "DOCK 4.0: search strategies for automated molecular docking of flexible molecule databases," Journal of Computer-Aided Molecular Design, vol. 15, pp. 411-428 (2001).
Garber, Ken, "Energy deregulation: licensing tumors to grow," Science, vol. 312, pp. 1158-1159 (2006).
Gohlke, Holger et al., "Knowledge-based scoring function to predict protein-ligand interactions," J Mol Biol, vol. 295, pp. 337-356 (2000).
Gottlieb, E. et al., "Mitochondrial tumour suppressors: a genetic and biochemical update," Nat Rev Cancer, vol. 5, pp. 857-866 (2005).
Guido, R.V. et al., "Virtual Screening and Its Integration with Modern Drug Design Technologies," Current Medicinal Chemistry, vol. 15, No. 1, pp. 37-46 (2008).
Hanks, S.K. et al., "The protein kinase family: conserved features and deduced phylogeny of the catalytic domains," Science, vol. 241, pp. 42-52 (1988).
Hsu, P.P. and D.M. Sabatini, Cancer cell metabolism: Warburg and beyond, Cell, vol. 134, No. 5, pp. 703-707 (2008).
Hue, L. et al., "Fructose 2,6-bisphosphate and the control of glycolysis by growth factors, tumor promoters and oncogenes," Adv Enzyme Regul, vol. 33, pp. 97-110 (1993).
Jones, G. et al., "Development and validation of a genetic algorithm for flexible docking," Journal of molecular biology, vol. 267, No. 3, pp. 727-748 (1997).
Jones, Russell G. et al., "Tumor suppressors and cell metabolism: a recipe for cancer growth," Genes Dev, vol. 23, pp. 537-548 (2009).
Kabsch, W., Xds. Acta Crystallogr D Biol Crystallogr, vol. 66, pp. 125-132 (2010).
Kim, S.G. et al., "A direct substrate-substrate interaction found in the kinase domain of the bifunctional enzyme, 6-phosphofructo-2-kinase/fructose-2,6-bisphosphatase," J. Mol. Biol., vol. 370, pp. 14-26 (2007).
Kim, J.W. et al., Cancers molecular sweet tooth and the Warburg effect. Cancer Research, vol. 66, pp. 8927-8930 (2006).
Kim, Song-Gun et al., "Crystal structure of the hypoxia-inducible form of 6-phosphofructo-2-kinase/fructose-2,6-bisphosphatase (PFKFB3): a possible new target for cancer therapy," J. Biol. Chem.,vol. 281, No. 5, pp. 2939-2944 (2006).
Klebe, Gerhard, "Virtual ligand screening: strategies, perspectives and limitations," Drug Discovery Today, vol. 11, No. 13-14, pp. 580-594 (2006).
Kroemer, Guido et al., "Tumor cell metabolism: cancers Achilles' heel," Cancer Cell, vol. 13, pp. 472-482 (2008).
Kruger, Dennis M. et al., "Comparison of Structure- and Ligand-Based Virtual Screening Protocols Considering Hit List Complementarity and Enrichment Factors," Chemmedchem, vol. 5, No. 1, pp. 148-158 (2010).
Kuntz, I.D., "Structure-based strategies for drug design and discovery," Science, vol. 257, pp. 1078-1082 (1992).

Lee, K. et al., "Pharmacophore modeling and virtual screening studies for new VEGFR-2 kinase inhibitors," European Journal of Medicinal Chemistry, vol. 45, No. 11, pp. pp. 5420-5427 (2010).
Li, Xun et al., "Evaluation of the Performance of Four Molecular Docking Programs on a Diverse Set of Protein-Ligand Complexes," Journal of Computational Chemistry, vol. 31, No. 11, pp. 2109-2125 (2010.
Maiorov, Vladimir et al., "Enhanced virtual screening by combined use of two docking methods: getting the most on a limited budget," J. Chem. Inf. Model., vol. 45, No. 4, pp. 1017-23 (2005).
Marsden, B.D. et al., "Doing more than just the structure-structural genomics in kinase drug discovery," Curr Opin Chem Biol, vol. 12, No. 1, pp. 40-45 (2008).
McConkey, David J., "Biochemical determinants of apoptosis and necrosis," Toxicol Lett, vol. 99, pp. 157-168 (1998).
Minchenko, Alexander et al., "Hypoxia-inducible factor-1-mediated expression of the 6-phosphofructo-2-kinase/fructose-2,6-bisphosphatase-3 (PFKFB3) gene. Its possible role in the Warburg effect," J Biol Chem, vol. 277, No. 8, pp. 6183-6187 (2002).
Minchenko, Oleksandr et al., "Hypoxic regulation of the 6phosphofructo2-kinase/fructose-2,6-bisphosphatase gene family (PFKFB-1-4) expression in vivo," FEBS Lett, vol. 554, pp. 264-270 (2003).
Nagarajan, Shanthi et al., "IKKβ inhibitors identification part II: Ligand and structure-based virtual screening," Bioorganic & Medicinal Chemistry, vol. 18, No. 11, pp. 3951-3960 (2010).
Nissler, K. et al., "Fructose 2,6-bisphosphate metabolism in Ehrlich ascites tumour cells," J Cancer Res Clin Oncol, vol. 121, pp. 739-745 (1995).
Parker, C.N. et al., "Towards unified compound screening strategies: A critical evaluation of error sources in experimental and virtual high-throughput screening," Qsar & Combinatorial Science, vol. 25, No. 12, pp. 1153-1161 (2006).
Pelicano, H. et al., "Glycolysis inhibition for anticancer treatment," Oncogene, vol. 25, pp. 4633-4646 (2006).
Perez, Juan J., "Managing molecular diversity," Chem Soc Rev, vol. 34, pp. 143-152 (2005).
Pilkis, Simon J. et al., "6-Phosphofructo-2-kinase/fructose-2,6-bisphosphatase: a metabolic signaling enzyme," Annu. Rev. Biochem., vol. 64, pp. 799-835 (1995).
Plewczynski, Dariusz et al., "Can We Trust Docking Results? Evaluation of Seven Commonly Used Programs on PDBbind Database," Journal of Computational Chemistry, vol. 32, No. 4, pp. 742-755 (2011).
Polyak, Kornella et al., "Somatic mutations of the mitochondrial genome in human colorectal tumours," Nat Genet, vol. 20, pp. 291-293 (1998).
Pouyssegur, Jacques et al., "Hypoxia signalling in cancer and approaches to enforce tumour regression," Nature, vol. 441, pp. 437-443 (2006).
Rarey, Matthias et al., "A fast flexible docking method using an incremental construction algorithm. Journal of molecular biology," vol. 261, No. 3, pp. 470-489 (1996).
Richter, Christoph et al., "Control of apoptosis by the cellular ATP level," FEBS Lett, vol. 378, pp. 107-110 (1996).
Rider, Mark H. et al., "6-phosphofructo-2-kinase/fructose-2,6-bisphosphatase: head-to-head with a bifunctional enzyme that controls glycolysis," Biochem. J., vol. 381, pp. 561-579 (2004).
Sousa, S.F. et al., "Virtual screening in drug design and development," Combinatorial Chemistry & High Throughput Screening, vol. 13, No. 5, pp. 442-453 (2010).
Swann, Steven L. et al., "A unified, probabilistic framework for structure- and ligand-based virtual screening," Journal of medicinal chemistry, vol. 54, No. 5, pp. 1223-1232 (2011).
Tan, Lu et al., "Integrating structure- and ligand-based virtual screening: comparison of individual, parallel, and fused molecular docking and similarity search calculations on multiple targets," Chemmedchem, vol. 3, No. 10, pp. 1566-1571 (2008).
Telang, S. et al., "Ras transformation requires metabolic control by 6-phosphofructo2-kinase," Oncogene, vol. 25, pp. 7225-7234 (2006).
Tennant, D.A. et al., "Targeting metabolic transformation for cancer therapy," Nat Rev Cancer, vol. 10, pp. 267-277 (2010).

(56) References Cited

OTHER PUBLICATIONS

The CCP4 suite: programs for protein crystallography. Acta Crystallogr D Biol Crystallogr 50: 760-763 (1994).

Trott, Oleg et al., "AutoDock Vina: improving the speed and accuracy of docking with a new scoring function, efficient optimization, and multithreading," Journal of Computational Chemistry, vol. 31, No. 2, pp. 455-461 (2010).

Tuccinardi, T., "Docking-Based Virtual Screening: Recent Developments," Combinatorial Chemistry & High Throughput Screening, vol. 12, No. 3, pp. 303-314 (2009).

van Engeland, M. et al., "Annexin V-affinity assay: a review on an apoptosis detection system based on phosphatidylserine exposure," Cytometry, vol. 31, pp. 1-9 (1998).

van Montfort, Rob L.M. et al., "Structure-based design of molecular cancer therapeutics," Trends in Biotechnology, vol. 27, No. 5, pp. 315-328 (2009).

Van Schaftingen, Emile et al., "Control of liver 6-phosphofructokinase by fructose 2,6-bisphosphate and other effectors," Proc Natl Acad Sci U S A, vol. 78, No. 6, pp. 3483-3486 (1981).

Van Schaftingen, Emile et aL, "A kinetic study of pyrophosphate: fructose-6-phosphate phosphotransferase from potato tubers. Application to a microassay of fructose 2,6-bisphosphate," Eur. J. Biochem., vol. 129, No. 1, pp. 191-195 (1982.

Vander Heiden, M.G. et al., "Understanding the Warburg effect: the metabolic requirements of cell proliferation," Science, vol. 324, pp. 1029-1033 (2009).

Villoutreix, B.O. et al., "Structure-Based Virtual Ligand Screening: Recent Success Stories," Combinatorial Chemistry & High Throughput Screening, vol. 12, No. 10, pp. 1000-1016 (2009).

Warburg, O., "On the origin of cancer cells," Science, vol. 123, pp. 309-314 (1956).

Xu, Rui-hua et al., "Inhibition of glycolysis in cancer cells: a novel strategy to overcome drug resistance associated with mitochondrial respiratory defect and hypoxia," Cancer Res, vol. 65, No. 2, pp. 613-621 (2005).

Yalcin, Abdullah et al., "Regulation of glucose metabolism by 6-phosphofructo-2-kinase/fructose-2,6-bisphosphatases in cancer," Exp. Mol. Pathol., vol. 86, No. 3, pp. 174-179 (2009).

Fujita, Shinsaku, "Enumeration of Alkanes as Stereoisomers," Communications in Mathematical and in Computer Chemistry, vol. 57, pp. 265-298 (2007).

Fujita, Shinsaku, "Numbers of Monosubstituted Alkanes as Stereoisomers," Journal of Computer Chemistry, Japan, vol. 6 No. 1, pp. 59-72 (2007).

\* cited by examiner

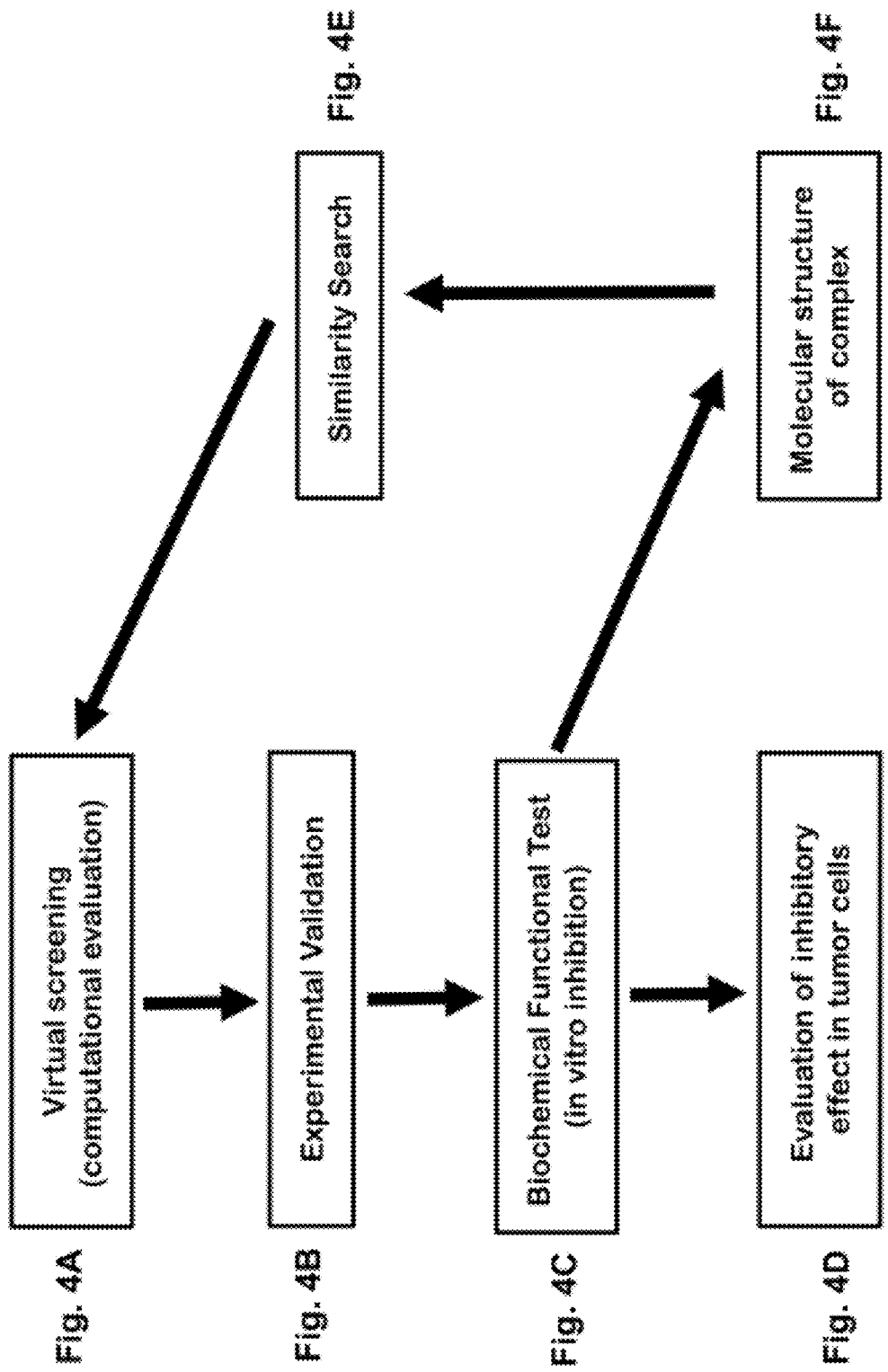

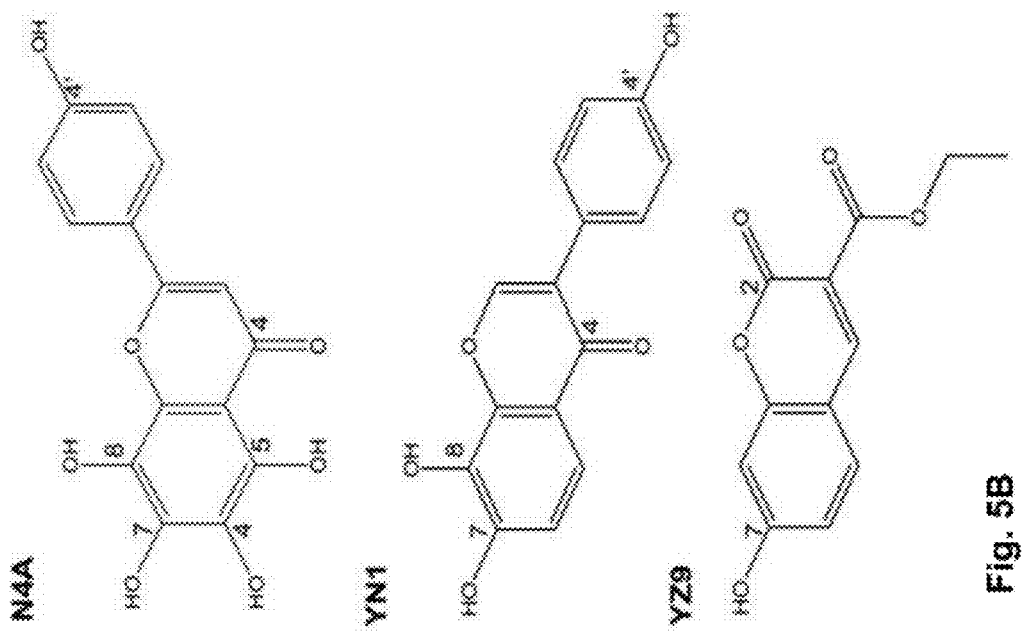
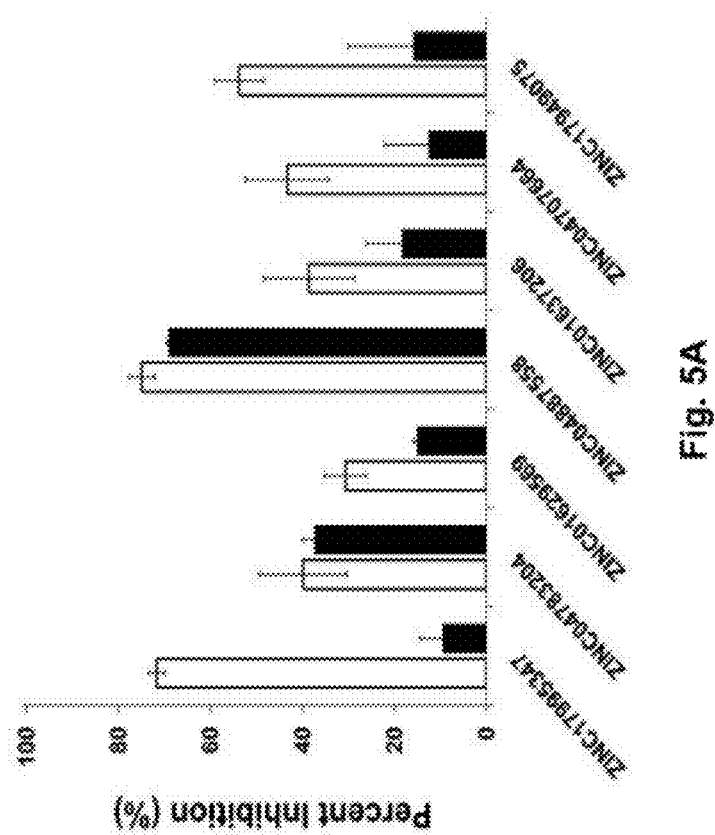
Fig. 5A
Fig. 5B

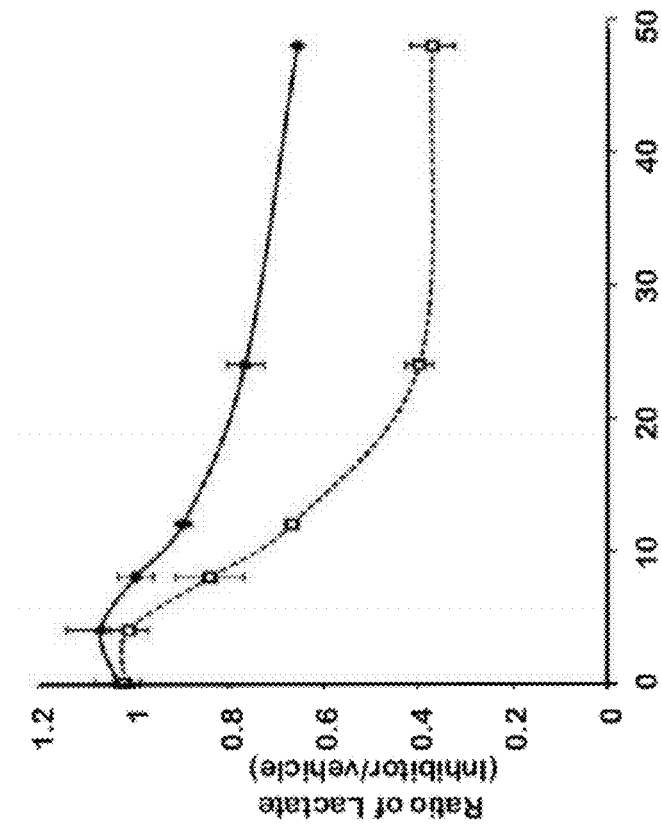
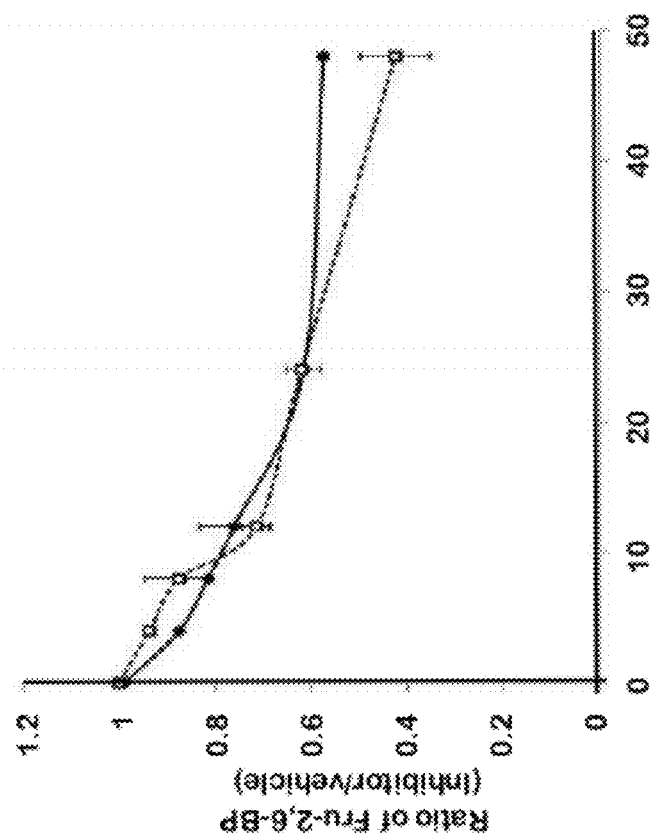
Fig. 6A
Fig. 6B

INHIBITORS OF PFKFB3 FOR CANCER THERAPY

CROSS-REFERENCE TO RELATED APPLICATIONS

This application claims priority under 35 U.S.C. §119(e) from U.S. Provisional Application Ser. No. 61/484,386, filed 10 May 2011, entitled "Inhibitors of PFKFB3 For Cancer Therapy," the contents of which are fully incorporated by reference herein.

STATEMENT REGARDING FEDERALLY SPONSORED RESEARCH OR DEVELOPMENT

This invention was made with government support under grant number R01CA124758-01A2 awarded by the National Institutes of Health. The Government has certain rights in the invention.

FIELD OF THE INVENTION

This invention relates to inhibitors of mammalian energy metabolism, more particularly it relates to compounds used to inhibit one of the isozymes of 6-phosphofructo-2-kinase/fructose-2,6-bisphosphatases (PFKFBs) involved in glycolysis, and more particularly it relates to inhibitors of isozyme (PFKFB3).

BACKGROUND ART

Glycolysis is the metabolic pathway in eukaryotes that converts glucose into pyruvate. The free energy released in this process is used to form the high-energy compounds ATP (adenosine triphosphate), $FADH_2$ and NADH (reduced nicotinamide adenine dinucleotide). Glycolysis is regulated by slowing down or speeding up certain steps in the glycolytic pathway, by inhibiting or activating the enzymes that are involved.

Phosphofructokinase is an important control point in the glycolytic pathway, since it is one of the irreversible steps and has key allosteric effectors. In the glycolysis pathway, phosphofructokinase-1 (PFK-1) catalyzes the major rate-limiting step that converts fructose-6-phosphate (Fru-6-P) to fructose-1,6-bisphosphate (Fru-1,6-BP). PFK-1 is allosterically regulated by fructose-2,6-bisphosphate (Fru-2,6-BP). Fru-2,6-BP is the most potent glycolysis stimulator.

Normally, under abundant energy supply, high levels of ATP strongly inhibit PFK-1 activity. However, Fru-2,6-BP can override this inhibitory effect and enhance glucose uptake and glycolytic flux. Of note, Fru-2,6-BP synthesis is up-regulated in many cancer cell lines.

Unlike normal cells, cancer cells have been noted to shift their energy metabolism toward glycolysis [34]. This phenomenon was originally termed the Warburg effect. This energy transition allows cancer cells to satisfy increased biosynthetic requirements for biomass and energy [35, 36]. Studies have consistently shown an abnormally high glycolytic rate in a wide spectrum of human cancers, but the causative mechanisms responsible for this metabolic adaptation remain poorly understood [37, 38]. Among the possible mechanisms, mitochondrial respiratory defects and hypoxia in the tumor microenvironment are attributed as two major factors for the Warburg effect [39, 40, 41].

Despite the complexity and obscurity of underlying mechanisms responsible for the Warburg effect, the metabolic consequences are a consistent transformation toward glycolysis as the major source of ATP production [37, 42]. This metabolic abnormality of cancer cells provides a potential biochemical basis to preferentially suppress progression of malignant cells by selective inhibition of glycolysis [43, 44, 45].

The upregulation of Fru-2,6-BP synthesis in many cancer cell lines has led to the suggestion that selective depletion of intracellular Fru-2,6-BP in cancer cells might be used to impede glycolytic flux, and thereby suppressing malignant cell survival and progression [49, 50, 51] A family of bifunctional enzymes, 6-phosphofructo-2-kinase/fructose-2, 6-bisphosphatases (PFKFBs; a family of 4 isozymes, i.e., PFKFB isozymes 1-4), are responsible for the intracellular levels of Fru-2,6-BP [51, 52, 53]. Among these isozymes, PFKFB3 is dominantly over-expressed in thyroid, breast, colon, prostatic, and ovarian tumor cell lines [51, 54, 55]. PFKFB3 has kinase activity at least 10× that of the second most active isoform, and rapidly increases the level of Fructose-2,6-bisphosphate (F-2,6-BP).[15, 16] Recent studies have shown that induction of PFKFB3 expression by HIF-1 under hypoxic condition was followed by increased invasive potential and resistance to chemotherapies [54, 56].

Accordingly, an area of unmet need has been the ability to inhibit PFKFB3 as a therapeutic strategy for cancer [55]. Despite the potential merits, exploitation of the inhibition of PFKFB3 for cancer therapy has remained an unmet need. A pyridinyl-containing compound has been reported as a possible PFKFB3 inhibitor, based on the receptor structure predicted from that of PFKFB4 [57; see also, U.S. Published Patent Application No. 2009/0074884]. Although promising, inhibitors based on structures other than the potent PFKFB3 enzyme may lack specificity and limit desired improvement of inhibitor potency.

BRIEF SUMMARY OF THE INVENTION

We have identified inhibitors of PFKFB3 based in part on the structure of the isozyme, and have confirmed this inhibition and the use of the inhibitors as cancer therapeutics using known cancer cell lines. We have studies the structure of PFKFB3 itself, as well as PFKFB3 in complex with its ligands, and based on the structural studies identified compounds that might act as inhibitors of PFKFB3. For example, the molecules termed N4A (5,6,7,8-tetrahydroxy-2-(4-hydroxyphenyl)chromene-4-one; NSC76988) and RBC2 ((Z)-ethyl 3-((1,4-dihydroxynaphthalen-2-yl)thio)but-2-enoate; NSC278631) were identified as a novel competitive inhibitor of PFKFB3 activity. Thereafter, the inhibition efficacy of the N4A was improved by use of structure-guided optimization. Using a similar approach, additional PFKFB3 inhibitors were identified, e.g., YN1 (7,8-dihydroxy-3-(4-hydroxyphenyl)chromen-4-one) and YZ9 (ethyl 7-hydroxy-2-oxochromene-3-carboxylate). As summarized in Table 1, all four compounds exhibited inhibition for PFKFB3 and inhibited the growth of cancer cells. YN1 exhibits $IC50=0.67$ μM and Ki=0.24±0.03 μM, showing a 5-fold increase in inhibition. Compound YZ9 shows even greater inhibition—one order of magnitude over the starting lead, N4A. All the tested compounds are soluble in various aqueous solutions up to 50 μM ranges in the presence of <1% dimethyl sulfoxide (DMSO).

The compounds N4A and YN1 were tested for their inhibitory effects on other human PFKFB isoforms. The inhibitors had a stronger effect on PFKFB3 than on other PFKFB isoforms. At twice the IC50 for PFKFB3 where PFKFB3 was over 80% inhibited, N4A exhibits less than 50% inhibition and YN1 shows less than 40% inhibition on PFKFB1, PFKFB2 and PFKFB4 (FIG. 8E). Advantageously, N4A and YN1 were found to be comparatively selective inhibitors of the potent isoenzyme PFKFB3.

Based on the above findings and in particular a structural analysis of the binding of N4A and YN1 to PFKFB3, we have identified other compounds or molecules that are believed to inhibit PFKFB3. These additional compounds are shown below in Tables 4-9. We believe that these compounds can be used to inhibit 6-phosphofructo-2-kinase/fructose-2,6-bisphosphatase (PFKFB), primarily the isozyme PFKFB3. In addition, these compounds of the invention may inhibit at least one of the other isozymes PFKFB1, PFKFB2, or PFKFB4. Compounds of the invention are used to preferentially inhibit isozyme PFKFB3, relative to other PFKFB isozymes. Compounds of the invention are used therapeutically to treat a patient with a disease in which the symptoms would be improved by inhibiting glycolytic metabolism, for example, one caused by growing cells, tissue or tumors that are preferentially dependent on glycolytic metabolism, for example, most cancer cells or tumors. It is understood that a therapeutic use does not require a cure; e.g., a remediation of a symptom, shortening/lessening of a disease course or prolongation of survival are within the definition of a therapeutic use.

BRIEF DESCRIPTION OF THE DRAWINGS

FIGS. 4A-4F show a flowchart that shows the overall strategy used for development of the PFKFB3 inhibitors.

FIGS. 5A-5E illustrate the experimental evaluation of three of the inhibitors, N4A, YN1 and YZ9. FIG. 5A shows the inhibition potencies of three of the candidate compounds. The magnitudes of inhibition by compounds at 10 µM each are measured through the enzyme assay and presented as percentiles against the control (□). The same experiment was also performed in the presence of 0.1% Tween-20 (■), to eliminate false positives caused by non-specific hydrophobic interactions. FIG. 5B shows the structures of three of the identified PFKFB3 inhibitors, N4A, YN1, and YZ9. FIG. 5C illustrates Lineweaver-Burk plots showing the competitive inhibition by N4A against Fru-6-P. The inhibitor concentrations used were: 0 µM (■), 1 µM (○), 2 µM (▲), and 3 µM (□) of N4A. They are also labeled next to individual plots. FIG. 5D shows the Lineweaver-Burk plots showing the competitive inhibition by YN1 against Fru-6-P. The inhibitor concentrations used were: 0 µM (■), 1 µM (○), 2 µM (▲), and 3 µM (□) of YN1. FIG. 5E shows the selectivity of N4A and YN1 on the four PFKFB isoforms. Results are expressed as percent inhibition at twice the $IC_{50}$ concentration against PFKFB3 (N4A=6 µM, YN1=1.3 µM).

FIGS. 6A-6C illustrate the effects of the PFKFB3 inhibitors on Fru-2,6-BP levels, lactate secretions, and cell growth. The Fru-2,6-BP levels (FIG. 6A) and the levels of secreted lactate (FIG. 6B) were determined enzymatically at time points 0, 4, 8, 12, 24, or 48 hours after the inhibitor treatments of HeLa cancer cells. The results were normalized to the sample protein concentrations and expressed as a ratio to the value of vehicle-treated. Data are means±S.E.M. from at least three experiments. Time-dependent effects of 25 µM each of N4A (—◆—) and YN1 (--□--) on the cellular Fru-2,6-BP levels (FIG. 6A) and the lactate secretions (FIG. 6B) are shown. FIG. 6C shows the growth inhibition by N4A, YN1, and YZ9 on HeLa and T47D cells. Cell numbers were assayed over 36 hours by the trypan blue counting or XTT assay. Data points are expressed as % cell growth of control containing vehicle against logarithmic scale of inhibitor concentrations. Error bars stand for intra-experimental replicates standard deviation.

FIG. 7A illustrates micrographs of anchorage-independent cell growth in soft agar. HeLa cells were grown in soft agar for 21 days in the presence of the indicated concentrations of N4A and YN1 respectively (20×). FIG. 7B shows the number of colonies under the various treatments, with the mean and S.D. shown (n=5).

FIG. 8A shows the induced cell death at two different concentrations of N4A as measured by flow cytometry after double staining with Annexin V and PI. FIG. 8B shows the increase in cell death from the flow-cytometric data (mean±SD) showing a dose-related effect of N4A. FIG. 8C shows the induced cell death at two different concentrations of YN1 as measured by flow cytometry after double staining with Annexin V and PI. FIG. 8D shows the increase in cell death from the flow-cytometric data (mean±SD) showing a dose-related effect of YN1.

DETAILED DESCRIPTION OF THE INVENTION

Figure 1:
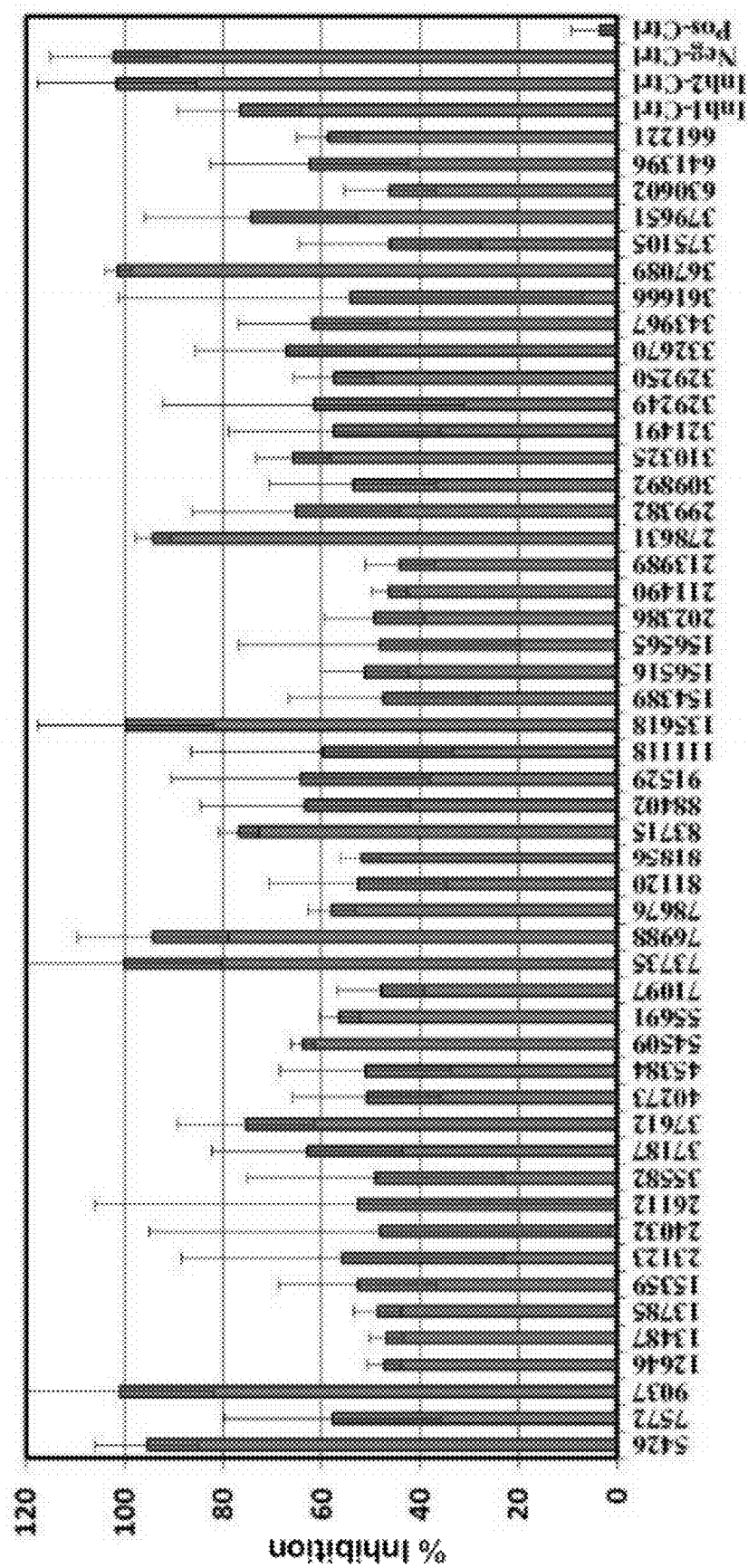
FIG. 1 illustrates the identification of potent PFKFB3 inhibitors via a single-dose (10 µM) primary screening assay. The top 50 PFKFB3 inhibitors of NCI's Diversity set II are shown in relation to four experimental controls with an average and standard deviation (S.D.) Inh1 and inh2 are in-house inhibitors that have been tested and shown to target PFKFB3 kinase domain. The controls, Pos and Neg, depict the uninhibited presence and complete absence of PFKFB3, respectively, and thus were used to represent the theoretical maximum and minimum inhibition values by which all screening compounds were compared.

Suppression of anaerobic glycolysis has been suggested as a promising strategy for the development of chemotherapeutic agents for conditions such as cancer which involve preferential use of or upregulation of glycolytic energy metabolism, For example, malignant tumor cells exhibit an abnormally high glycolytic rate even in the presence of oxygen [43, 44, 45, 55]. The rate of glycolysis is regulated by the cellular concentration of Fru-2,6-BP, a potent stimulator of glycolysis [46, 47, 48]. Recent studies invariably show that Fru-2,6-BP production is increased in transformed cell lines due to the expression of PFKFB3, the hypoxia-inducible isoform of the 6-phosphofructo-2-kinase/fructose-2,6-bisphosphatases, that catalyzes the synthesis of Fru-2,6-BP at least ten times greater rate than other isoforms [50, 51, 53, 54, 55].

To better understand the molecular mechanism of inhibitor-recognition by PFKFB3, we determined the structure of the PFKFB3 in complex with N4A. Guided by the structural basis for inhibitor binding, N4A was optimized using similarity search and computational evaluation, resulting in additional compound embodiments with, e.g., 5-fold improvement in potency.

In addition, inhibition of Fru-2,6-BP production and glycolysis in HeLa cells by the identified PFKFB3 inhibitors was evaluated. The newly identified inhibitors of PFKFB3 reduced the Fru-2,6-BP levels and glycolytic flux, resulting not only in growth inhibition of tumor cells but also massive cell death. These results validated targeting of PFKFB3 and set forth for the first time in the art direct structural insights into the protein inhibitor interactions. The present disclosure enables structure-assisted design and development of novel PFKFB3 inhibitors as modulators of the glycolytic pathway and as chemotherapeutic agents for cancer.

To evaluate PFKFB3, we determined the crystal structure of PFKFB3 to 2.1 Å and elucidated the catalytic mechanism for F-2,6-P2 synthesis at the molecular level.[20] The resulting molecular structure/function information was used as the foundation in order to develop data herein. Six out of a total 1,364 compounds from NCI's Diversity Set II were selected as true actives via throughput screening.

Using a database constructed from these compounds, five programs were tested for structure-based docking performance, of which, Chemical Computing Group's Molecular Operating Environment (MOE) showed the highest enrichments and second highest screening rates. Separately, using the same database, pharmacophore screening was performed, reducing 1,364 compounds to 287 with no loss in true actives, yielding an enrichment of 4.75. When structure-based docking was retested with the pharmacophore filtered database, 4 of the 5 structure-based docking programs showed significant improvements to enrichment rates at only 2.5% of the database, with a 7-fold decrease in an average virtual screening time. Our results altogether suggest that combinatorial approaches of virtual screening technologies are easily applicable to small molecule kinases and, moreover, that such methods can decrease the variability associated with single-method structure-based docking approaches.

In addition, we set forth several embodiments of molecules that inhibit the glycolytic pathway; inhibit a PFKFB enzyme, in particular the PFKFB3 isozyme, and serve as therapeutics for pathologic conditions characterized by a preference for or upregulation of glycolysis, such as certain cancers.

Example 1

Efficacy of Combinatorial Approaches in Virtual Screening PFKFB3 Inhibitors

To identify inhibitors of PFKFB3, a cancer therapeutic target, we determined the crystal structure of PFKFB3 to 2.1 Å and elucidated the catalytic mechanism for F-2,6-P2 synthesis at the molecular level.[20] The resulting molecular structure/function information was then used as described herein. For additional information, see Crochet et al., "Investigating combinatorial approaches in virtual screening on human inducible 6-phosphofructo-2-kinase/fructose-2,6-bisphosphatase (PFKFB3): A case study for small molecule kinases," Analytical Biochemistry, vol. 418(1), pp. 143-148 (2011; available online 2 Jul. 2011), which is incorporated by reference in its entirety into this application.

We investigated the efficacy of combinatorial screening of PFKFB3 targeting for the F-6-P site. To evaluate the efficacy of our tiered approach, we developed our own database of active/non-active molecules from the National Cancer Institute's (NCI) Diversity Set II through a biochemical throughput study. Using the actives as reference compounds, we explored applications from the two most common approaches in computational drug discovery: pharmacophore screening and structure based docking. Herein, we demonstrated the enrichment of a 1,364 compound database, containing six true actives 'T-actives', to a resultant database of 287 compounds, still containing six 'T-actives', while using only one seventh of the computational resources required for standard docking procedures.

Accordingly, in this example, we demonstrated that the combined use of ligand- and structure-based screening for small molecule kinases can decrease screening times and increase enrichment rates as compared with single step screening approaches.

Biochemical Throughput Screening.

To generate a framework of actives and non-actives for virtual screening, a throughput study of 1,364 NCI compounds was carried out. The inhibition extent of 10 $\mu$M of each compound, in substrate saturation conditions, was quantified and the results of the top 50 compounds are shown in FIG. 1. An arbitrary cutoff was chosen at 75% inhibition to describe compounds that were to be considered 'potential' actives. Based on this cutoff, 10 compounds were identified from the original 1,364.

Figure 2:
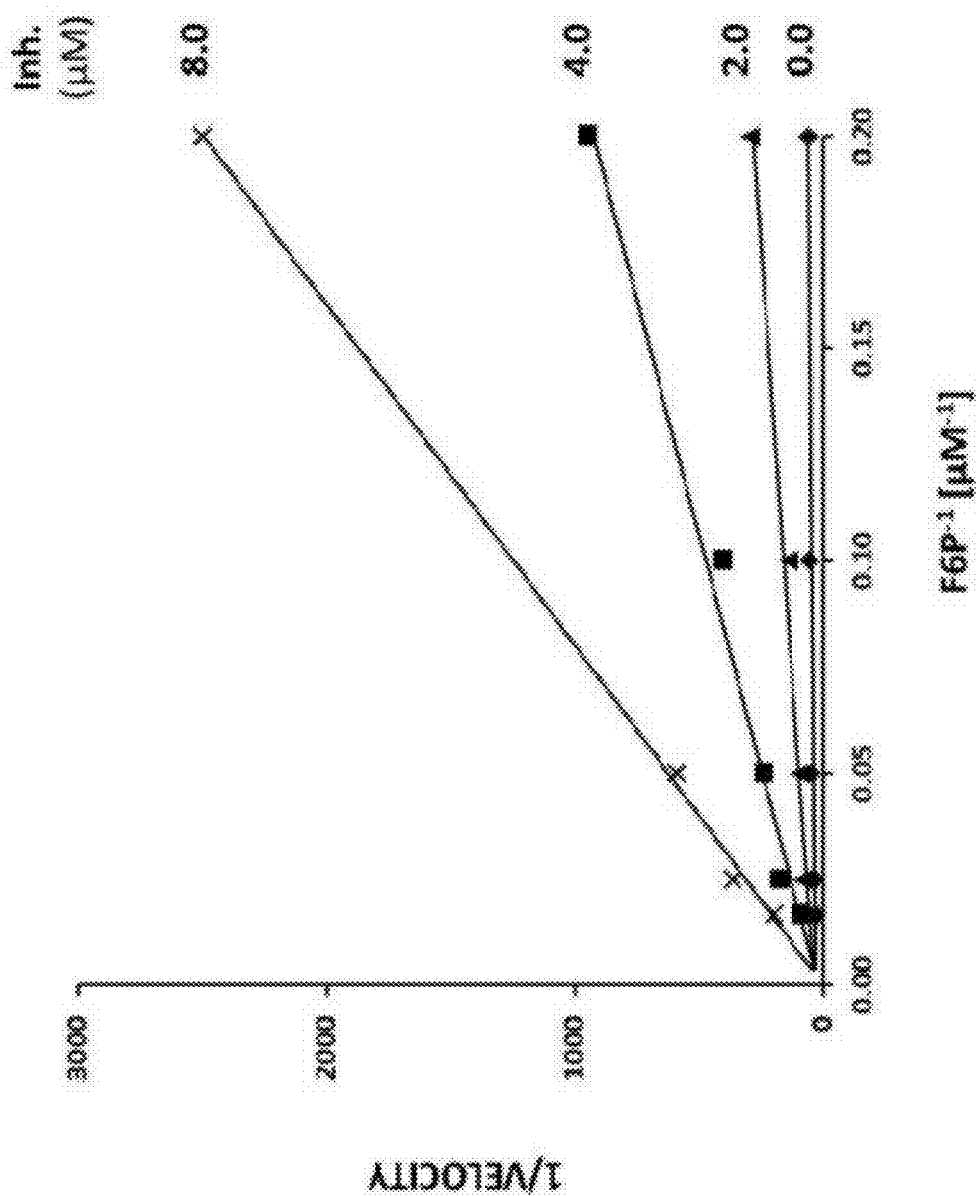
FIG. 2 illustrates the inhibition for the PFKFB3 2-kinase by NSC278631. A double-reciprocal plot shows the competitive inhibition for RBC2 (NSC278631) against F-6-P. The lines represent varying inhibitor concentrations and were generated by data fitting using the program GraphPad Prism [33].
Figure 3:
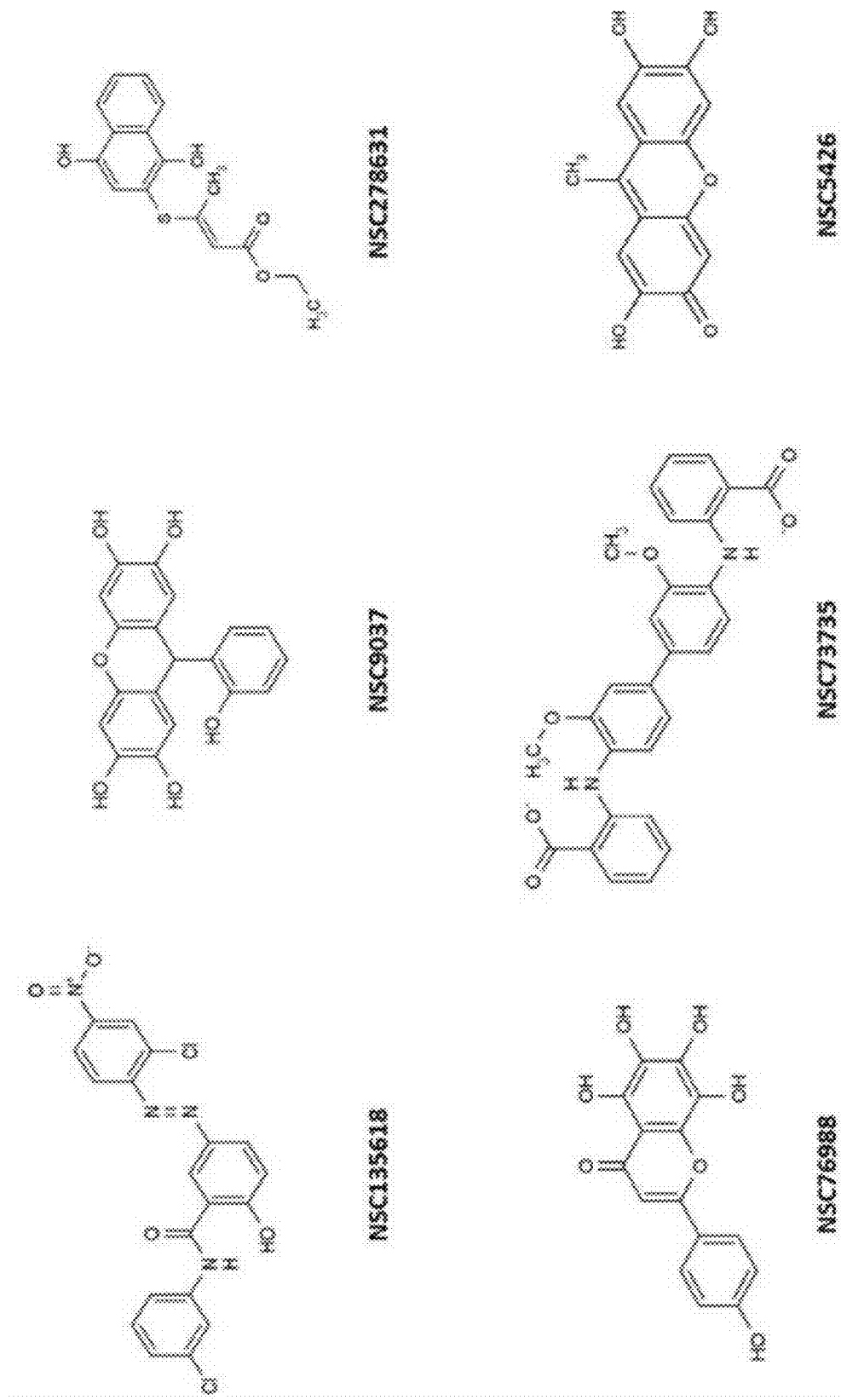
FIG. 3 illustrates the structures of a few selected active compounds from the throughput screening of the NCI Diversity Set II. For example, the molecules termed N4A (5,6,7,8-tetrahydroxy-2-(4-hydroxyphenyl)chromene-4-one; NSC76988) and RBC2 ((Z)-ethyl 3-((1,4-dihydroxynaphthalen-2-yl)thio)but-2-enoate; NSC278631) are shown.

To select the true positives, the 10 potential actives were subsequently tested for specificity for the F-6-P site, because the virtual screening was targeted for the F-6-P site. Using conventional steady state inhibition kinetics, 6 compounds were selected as the 'true actives' (T-actives), and these six compounds are shown in FIG. 3. All T-actives exhibited competitive inhibition against F-6-P and uncompetitive activity against ATP. For example, as a representative example, RBC2 (NSC278631) is shown in FIG. 2. The Ki's for each compound was determined to be at or below 20 $\mu$M.

Pharmacophore Screening.

Using ligands already known to bind to the F-6-P site from crystallographic evidence, namely, F-6-P [27]; F-2,6-P2 [27]; EDTA[20], and PEP [27], a pharmacophore model was built and used to screen the NCI diversity set the using pharmacophore screening module of Chemical Computing Group's Molecular Operating Environment (MOE) program. Overall, from this filtering process, the database size was reduced from 1364 to 287 ligands while retaining 6 out of 6 'T-actives'. The results of this procedure demonstrated a significant reduction in non-actives, and no reduction in actives.

Performance Comparisons of Docking Programs.

Because it has been demonstrated in numerous studies that the efficacy of a structure-based docking program directly ties to the target protein, the individual performances of several structure-based docking programs were tested. Using PFKFB3, a full database evaluation was conducted to compare the enrichment factors of five popular structure-based docking technologies. The results revealed that each of the tested structure-based docking technologies significantly enriched the NCI diversity set II database. However, as seen in other studies, the enrichment rates varied significantly according to the structure-based docking technology.[28-30] For comparison purposes, we investigated the enrichment at two database sizes, 2.5% and 10%. MOE performed the best, showing higher enrichments at all database sizes. The other structure-based docking programs were more varied in their performances with VINA having the second highest enrichment rates at 2.5% and GOLD at 10%.

Combinatorial Screening Efficacies.

To measure the efficacy of the combinatorial screening protocol, the pharmacophore filtering results were subsequently docked using each of the structure-based docking technologies. For this, the pharmacophore screening enriched database, consisting of the 287 hit molecules with all actives present, was docked and the enrichment rates were evaluated at 2.5% and 10% database sizes. The results demonstrate improved enrichment rates for four of the five SBG technologies at 2.5% database size and five of five at 10% database size compared with docking-only methods. Additionally, it was determined that the application of the combined protocol, greatly reduced the variability of the incorporated structure-based docking technologies, changing the enrichment differences between the highest and lowest scoring technologies from 13 to 6.5 and 4.9 to 3.2 at 2.5% and 10% database sizes, respectively. Reductions in the overall time were also witnessed, showing nearly a 7-fold decrease in the average total time for a complete database screening using the tiered approach.

Materials and Methods for Example 1.

Biochemical Throughput Screening.

The recombinant human PFKFB3 was expressed and purified as previously described.[20] The 1,364 individual compounds of NCI's Diversity Set II were acquired from the NCI.

The 2-kinase activity assay for throughput screening was performed using a F-2,6-P2 assay modified for 96-well plates from the conventional method.[21] This assay consisted of two sequential steps: F-2,6-P2 production by PFKFB3 and allosteric activation of PFK-1 by produced F-2,6-P2. The first reaction, F-2,6-P2 synthesis by PFKFB3, was started by adding 130 nM PFKFB3 to mixtures containing 20 mM pH 8.0 TES, 1 mM DTT, 2 mM $MgCl_2$, 50 µM F-6-P, 50 µM ATP, 0.5% Tween, and 10 µM of each inhibitor. This reaction was allowed to run for 10 minutes at 25° C., and then stopped by the addition of 0.1 M KOH. Aliquots of 1-4 µL of the first reaction were transferred, after pH neutralization, to the reactions of the second step, which consisted of 50 mM pH 8.0 Tris-HCl, 0.2 mM NADH, 5 mM DTT, 1 mM F-6-P, 2 mM $MgCl_2$, 0.70 units/mL Aldolase, 0.45 units/mL GDH, 0.60 units/mL TIM, and 10 mU PPi: PFK. The reactions of seconds step were started by adding 0.5 mM sodium pyrophosphate (PPi) and were then measured for changes in absorbance at 340 nm over a period of 30 minutes. The compounds RBC2 ((Z)-ethyl 3-((1,4-dihydroxynaphthalen-2-yl)thio)but-2-enoate; NSC278631) and N4A (5,6,7,8-tetrahydroxy-2-(4-hydroxyphenyl)chromene-4-one); NSC76988) came from the National Cancer Institute as a component of the NCI Diversity Set II.

For molecules showing strong inhibition in the throughput assay, a study of the steady-state inhibition kinetics was carried out using a method in which the concentrations of F-6-P, ATP, and/or inhibitors were varied according to experimental purposes.

Ligand Library Design.

The virtual ligands of NCI's Diversity Set II were obtained from NCI's Developmental therapeutics program (DTP). The ligands were acquired in SMILEs format and standardized using a template to ensure that each was minimized, pH adjusted, and devoid of salts and other non-ligand contaminants. Additional adjustments, such as explicit hydrogens and force fields were added in a program-dependent fashion depending on manufacturer recommendations. Using the standardized ligand database, an additional conformer database was generated for pharmacophore filtering. For this, Molecular Operating Environment (MOE) was used to generate a conformer database based on default settings with a maximum of 250 conformers per ligand and no post-generation refinement.

Structure-Based Virtual Docking.

Virtual docking was carried out using 5 different programs, DOCK, VINA, FlexX, MOE, and GOLD in an effort to determine the suitability of each for PFKFB3 screening. [22-26] For this, the protein structure '2AXN' was used as the receptor macromolecule for docking.[20]

Pharmacophore Screening.

MOE was used to generate pharmacophores from three molecules known to bind to the F-6-P pocket of the PFKFB3: Fructose-6-Phosphate (F-6-P), Ethylenediaminetetraacetic acid (EDTA), and Phosphoenol Pyruvate (PEP). The conformations for these molecules were obtained from the structural data (PDB ID: 2AXN, 2DWO, 2I1V, 2DWP). By superimposing the conformers, property features were extracted and merged, and tolerance values were adjusted in accordance with results through retro-fitting. After refinement, eight features were chosen to be included in the final pharmacophore map; however, only 5 features are required to be met at any one time for a compound to pass the filter. Additionally, inclusion and exclusion spheres were added and constraint allowances were adjusted for preference. All pharmacophore searches were carried out within MOE.

Example 2

Structure-Based Development of Small Molecule PFKFB3 Inhibitors

A schematic flow diagram describing the present strategy for development of PFKFB3 inhibitors is shown in FIG. 4. Candidates were selected from computational screening using the crystal structure of PFKFB3, which we have previously determined to 2.1 Å resolution [58], as molecular sieve of screening (FIG. 4A). The resulting hit compounds from this molecular sieve were evaluated by enzymatic inhibition assay, and compounds with the highest inhibition activity were selected as "lead" embodiments in accordance with the invention after consideration of drug-likeliness (FIG. 4B). Next, detailed kinetic properties were characterized (FIG. 4C), and the biological effects on human cancer cells were investigated by measuring glycolytic flux, growth inhibition, and cell death (FIG. 4D). To understand the molecular basis of the inhibition of PFKFB3, X-ray crystallographic structure analysis of the PFKFB3.inhibitor complex was carried out (FIG. 4F). Based on the molecular information gained from Step (FIG. 4F), we performed a search for novel compounds with improved potency, using a "lead" compound as a template (FIG. 4E). The resulting compounds from this similarity search were evaluated through computational docking using FlexX [59], and the best-optimized compound was passed through this selection process again. For more information, see below, and see M. Seo et al., "Structure-based development of small molecule PFKFB3 inhibitors: a framework for potential cancer therapeutic agents targeting the Warburg effect," PLoS ONE, Vol. 6(9), e24179 (published online 21 Sep. 2011), which is incorporated by reference in its entirety into this application.

As shown below in Examples 3-5, through iterative cycles of these processes, compounds were obtained that had inhibitory activity orders of magnitude above the initial embodiments which had already exhibited potent PFKFB3 inhibition in vitro.

Accordingly, as shown below, we were able to introduce a potent competitive inhibitor of PFKFB3, N4A with an $IC_{50}$ of 2.97 µM. The inhibitor also shows a stronger effect on PFKFB3 than on other PFKFB isoforms. Despite high homology between PFKFB isoforms, the inhibitor has higher specificity for PFKFB3. As a result of proper targeting, the PFKFB3 inhibitor reduced the Fru-2,6-BP level and glycolytic rate in cells, ultimately, leading to tumor growth inhibition and massive cell death. The cell death induced by the inhibitor involved both apoptosis and necrosis. The present observation is coincident with previous reports that depletion of cellular energy tends to cause necrotic cell death, because apoptosis is an energy requiring process [44, 60, 61]. Supporting this idea, we found apoptotic cell death was primarily observed at a relatively low inhibitor concentration (25 µM), which would produce only moderate energy depletion (data not shown). On the other hand, higher concentration of inhibitors (50 µM) significantly increased both necrosis and apoptosis, leading to an insufficient energy state where the apoptotic process is not favored.

Although N4A and YN1 show comparatively selective PFKFB3 inhibition between the PFKFB isoforms, the antiproliferative effect of the inhibitors on cancer cells cannot be solely ascribed to the inhibition of PFKFB3 kinase activity. However, the development of N4A and YN1 provide embodiments of specific PFKFB3 inhibitors possessing high selectivity and low general toxicity.

Determination of protein structures in complex with an inhibitor is important in order to obtain mechanisms for inhibitor recognition at the molecular level and to provide an opportunity to identify alternative molecules with higher potency [65, 66]. Understanding the molecular basis for interactions between a potential drug molecule and its target protein is a critical step in successful drug development [66]. As set forth herein, the first molecular structure of PFKFB3 in complex with an inhibitor was determined, and then this was used to improve potency of additional inhibitors.

The crystal structures of PFKFB3 in complex with N4A revealed information on inhibitor binding at the molecular level. The crystal structure with YN1 provided an insight into alternative bindings of similar compounds. The two together provided embodiments of new compounds as well as rational guidelines for design of novel PFKFB3 inhibitors. Although YN1 is a derivative of the lead compound N4A and the binding modes of the two inhibitors are in approximately the same plane, it appeared, even at the modest resolution of the YN1 complex, that the interactions of these two compounds with PFKFB3 are quite different. The difference of orientations within the same Fru-6-P plane is likely the consequence of YN1 having a less bulky chromone moiety (two fewer hydroxyl groups compared to N4A). The new binding mode observed for YN1 results in new hydrophobic interactions and the addition of Cation-π interactions, which together compensate for the loss of hydroxyl groups, which participated in hydrogen bond in the N4A complex, and appear to support the higher inhibitory activity of YN1.

It is noteworthy that the present inhibitors, even though they lack negatively charged groups, efficiently targeted the Fru-6-P pocket, which is populated with positively charged residues. The accompanied energy penalty for such bindings is likely to be paid by increases in the Cation-π interactions. This hypothesis was tested with a third compound YZ9, which showed the inhibition potency increased by an order of magnitude.

Thus, the examples described below disclose PFKFB3 inhibitors, as well as an approach that enables the rational design of inhibitors which have higher specificities, e.g., by targeting the Fru-6-P site instead of targeting the ATP site since the ATP site fold is shared by thousands of other kinases [67, 68].

Example 3

Inhibitor Screening and Binding Properties

Figure 5D:
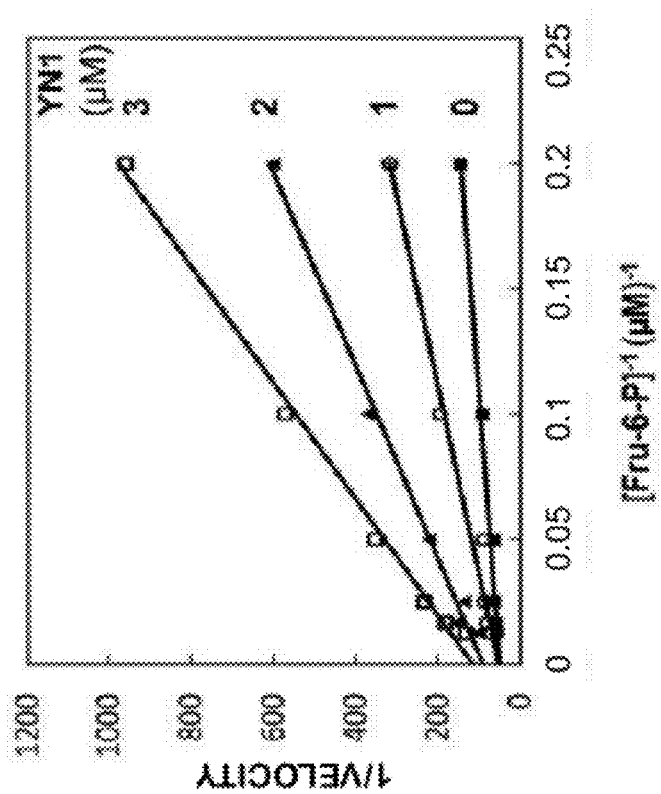
Figure 5C:
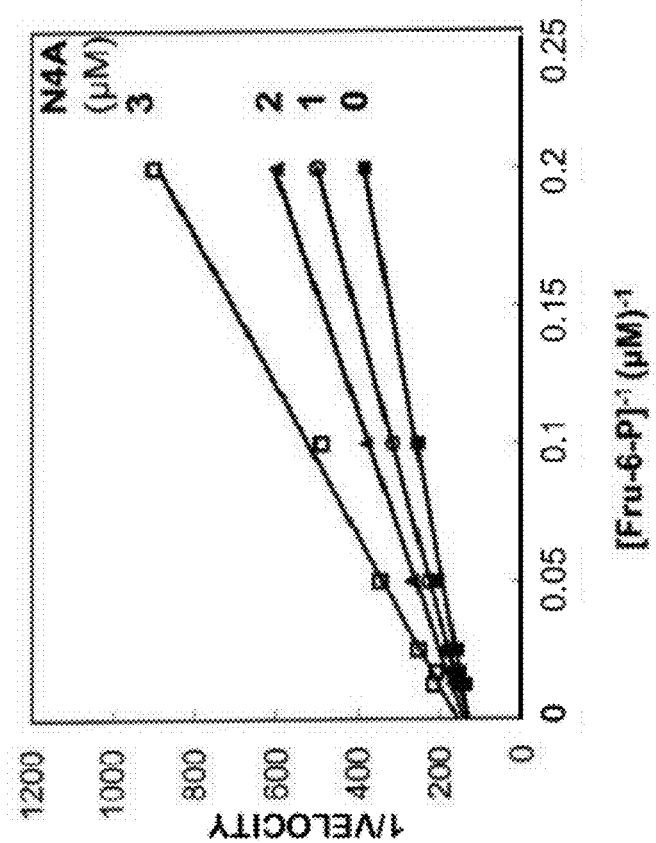
Figure 5E:
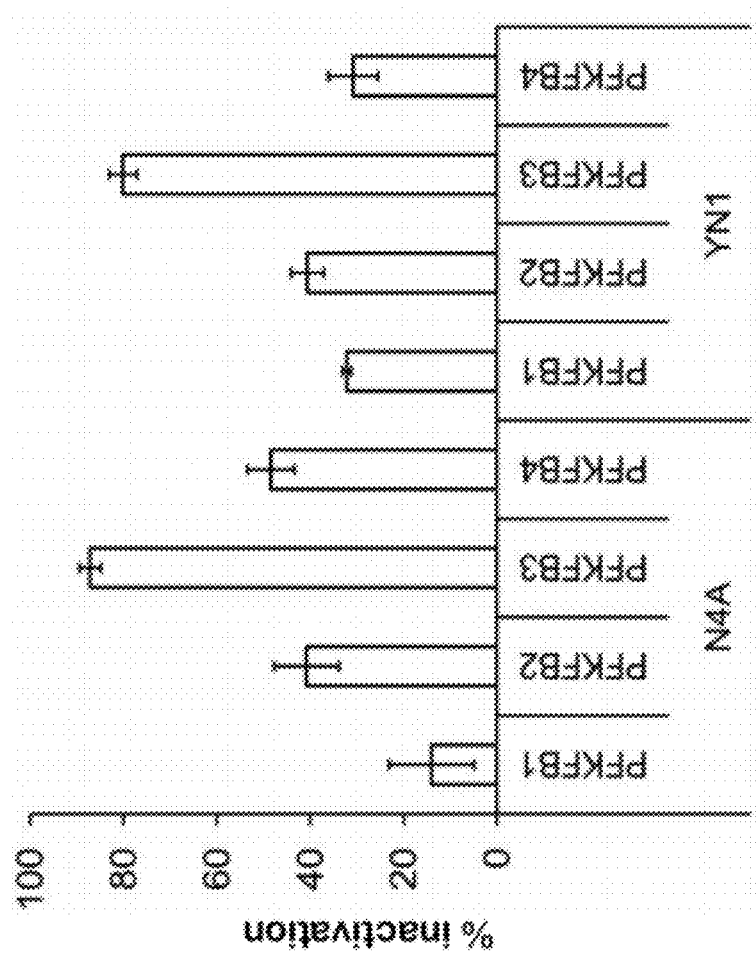

As set forth in Examples 1 and 2, several compounds capable of binding to the Fru-6-P pocket of PFKFB3 were identified from virtual screening (also see, Crochet et al., Anal Biochem. 2011 Nov. 1; 418(1):143-8). To confirm the inhibitory activities and to eliminate false positives from these drug candidates, PFKFB3 inhibition was tested at 10 µM each of several of the compounds (FIG. 5A). To prevent non-specific inhibition caused by random hydrophobic interactions between inhibitor and protein, a same test was performed in the presence of 0.1% Tween-20. Among the tested compounds, ZINC04887558 (N4A, 5,6,7,8-tetrahydroxy-2-(4-hydroxyphenyl)chromen-4-one) inhibited enzyme activity greater than 65% under substrate-saturating conditions, and this inhibition was not affected by the presence of Tween-20. We selected N4A as an initial 'lead', and its structure is shown in FIG. 5B. The subsequent kinetic study revealed that N4A inhibits PFKFB3 with an $IC_{50}$ value of 2.97±0.16 µM (Table 1). A steady state inhibition study showed that N4A inhibits PFKFB3 as a competitive inhibitor against Fru-6-P with a Ki of 1.29±0.26 µM, as expected from virtual screening and as demonstrated in a Lineweaver-Burk plot (FIG. 5C). Similar studies were conducted using YN1, and the results are shown in Table 1 and FIG. 5D. In addition, the inhibition of N4A and YN1 on all four isozymes of PFKFB was tested, and the results shown in FIG. 5E. Although some inhibition was shown for all tested isozymes, as seen in FIG. 5E, the strongest inhibition was for PFKB3.

Example 4

Effects of N4A and YN1 on the Fru-2,6-BP Levels, Glycolysis, and Cell Growth

Thereafter, the effects of applying the inhibitor compounds N4A and YN1 to live HeLa cells, a human cervical cancer cell line, was evaluated. Inhibition of PFKFB3 was expected to cause a decrease in the levels of Fru-2,6-BP in HeLa cells. After an 8 hour exposure to N4A and YN1, the amount of Fru-2,6-BP (measured as a ratio to a control) was reduced approximately 20%; after a 48-hour exposure, Fru-2,6-BP was reduced over 40% (FIG. 6A). Down-regulation of the Fru-2,6-BP levels by N4A and YN1 was accompanied by decreased glycolysis, as expected. The decrease in the Fru-2,6-BP levels following exposure to N4A and YN1 led to a decrease in lactate production, which was reflected by a greater than 30% decrease in lactate secretion, as shown in FIG. 6B. Taken together, FIGS. 6A and 6B show that N4A and YN1 inhibit PFKFB3, and this inhibition results in a suppression of glycolysis.

Figure 6C:
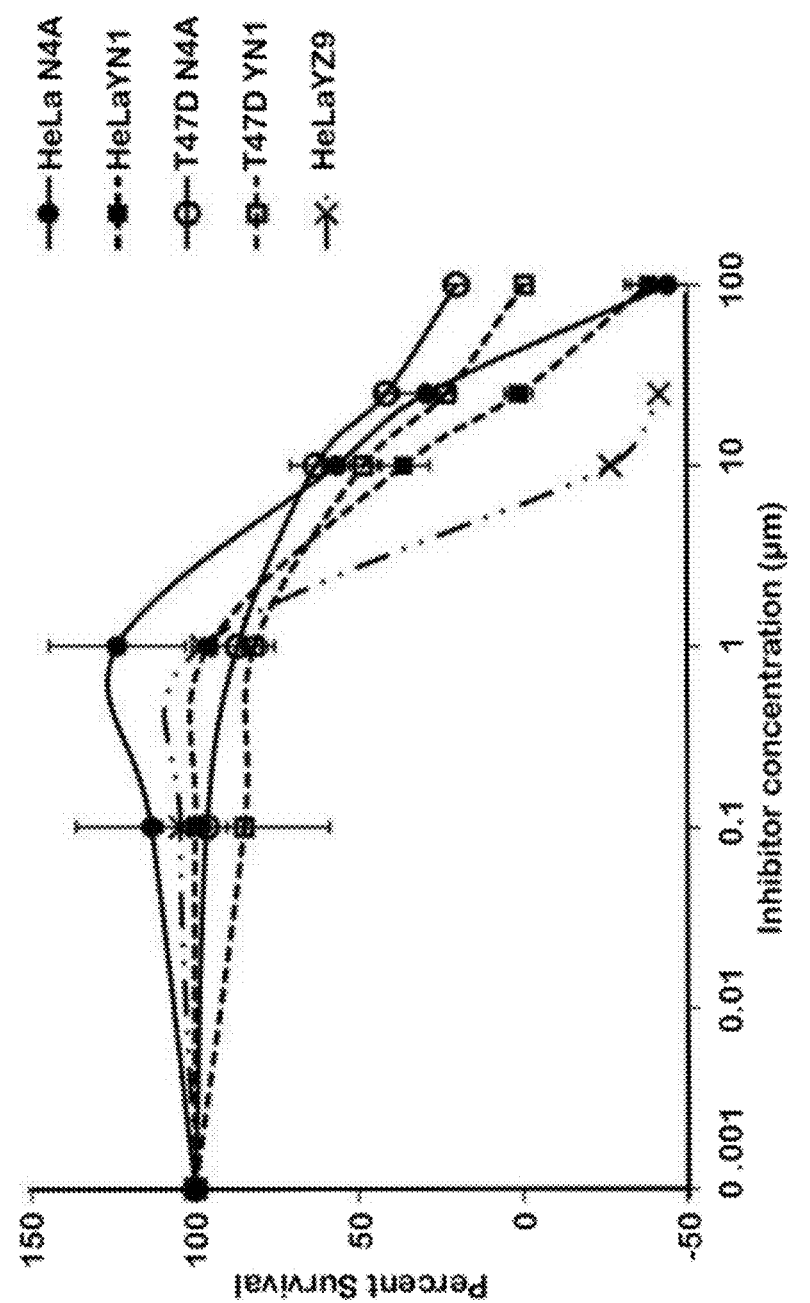

An increase in Fru-2,6-BP levels and increased glycolysis often accompanies the proliferation of transformed cells, including cancer cells [36]. Accordingly, the effect of PFKFB3 inhibitors, N4A, YN1, YZ9 and RBC2, on the proliferation rate of one or more of human cervical cancer cells (HeLa) and human breast cancer cells (T47D or MCF-7) were examined. Treatments with 25 µM each of N4A, YN1 and YZ9 caused significant reduction in cell survival as compared to unexposed cells (FIG. 6C). The results of cell growth inhibition assays confirmed that inhibition of PFKFB3 by N4A, YN1, and YZ9 suppressed cellular energy metabolism and, ultimately, cell growth and survival. Moreover these data showed that YN1 is a more potent growth inhibitor with a $GI_{50}$ of 8.2±0.8 µM compared with N4A ($GI_{50}$=14.2±1.5 µM) (Table 1). As shown in Table 1, the most potent growth inhibitors for the cancer cells were RBC2 and YZ9.

TABLE 1

The kinetic and biological properties of four PFKFB3 inhibitors.

| Inhibitor | $IC_{50}$ [µM] | $K_i$ [µM] | Inhibition | $GI_{50}$ [µM] |
|---|---|---|---|---|
| N4A | 2.97 ± 0.16 | 1.29 ± 0.26 | Competitive to Fru-6-P | 14.2 ± 1.5 |
| YN1 | 0.67 ± 0.08 | 0.24 ± 0.03 | Competitive to Fru-6-P | 8.2 ± 0.8 |
| YZ9 | 0.18 | 0.094 | Competitive to Fru-6-P | 2.7 ± 0.2 |
| RBC2 | | 0.078 | Competitive to Fru-6-P | 3.5 (T47D) |
| | | | | 4.4 (MCF7) |

Figure 7A:
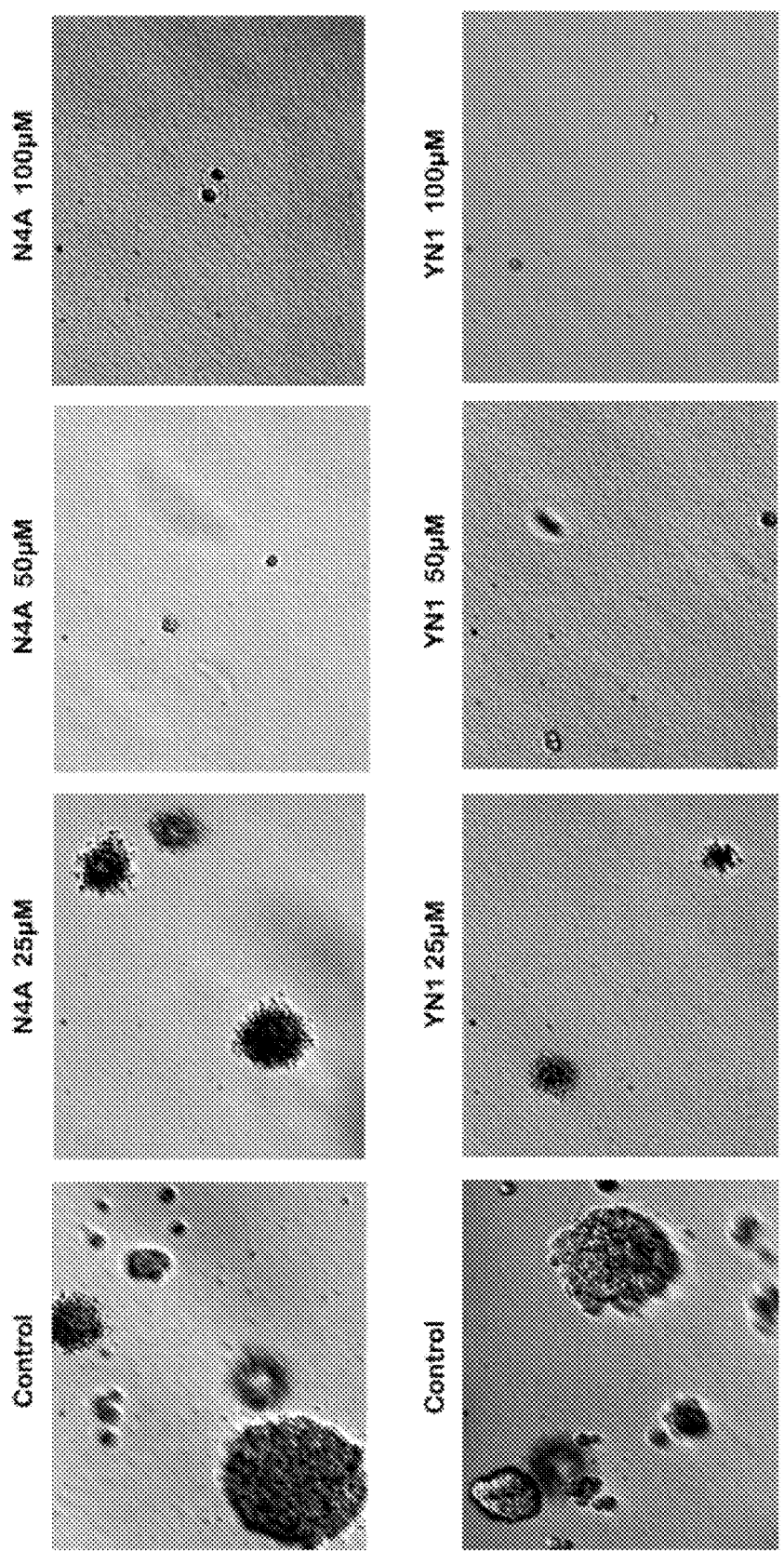
FIGS. 7A and 7B show that the treatment of HeLa cells with either N4A or YN1 inhibits soft agar colony formation.
Figure 7B:
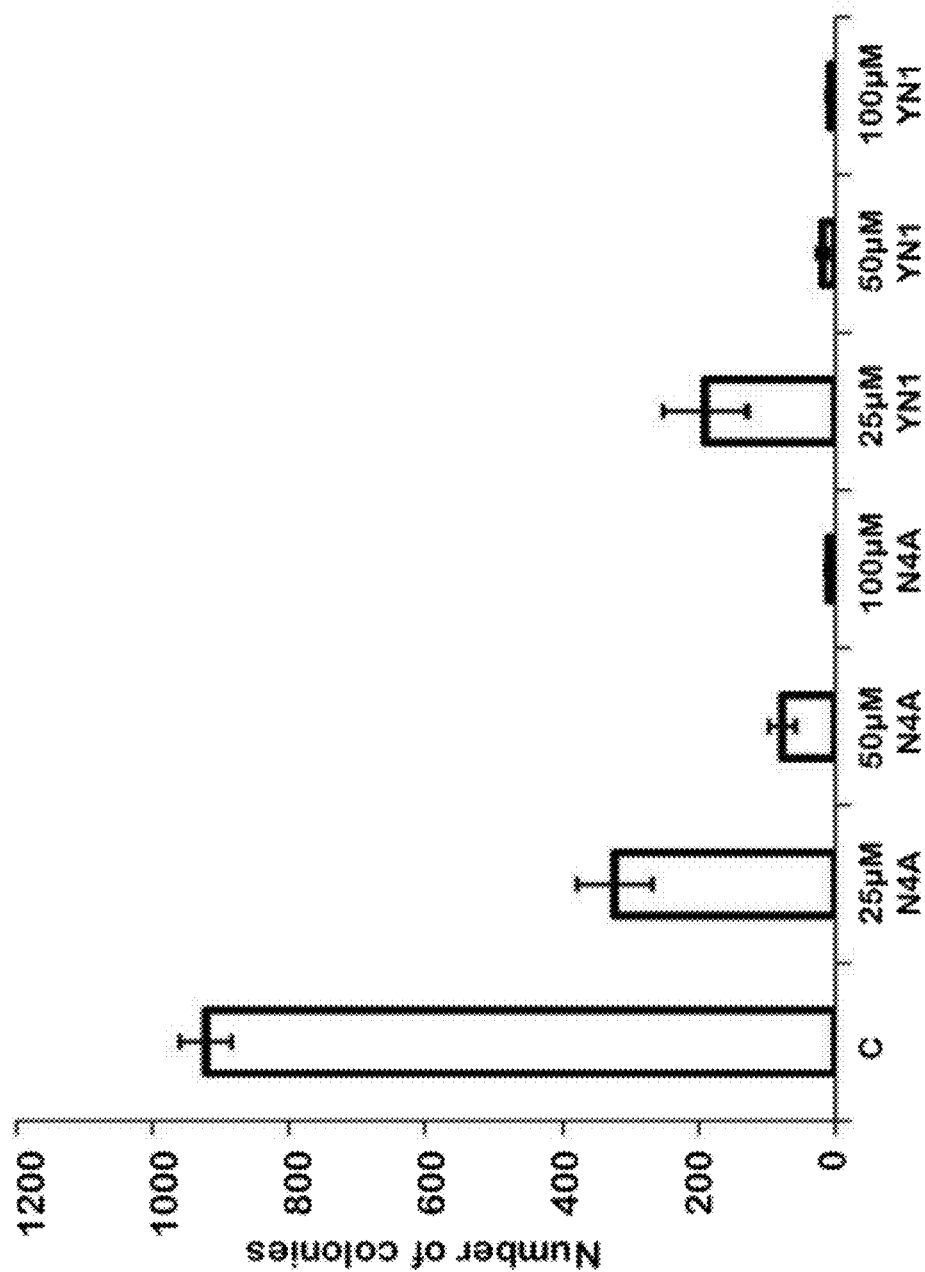
Figure 8A:
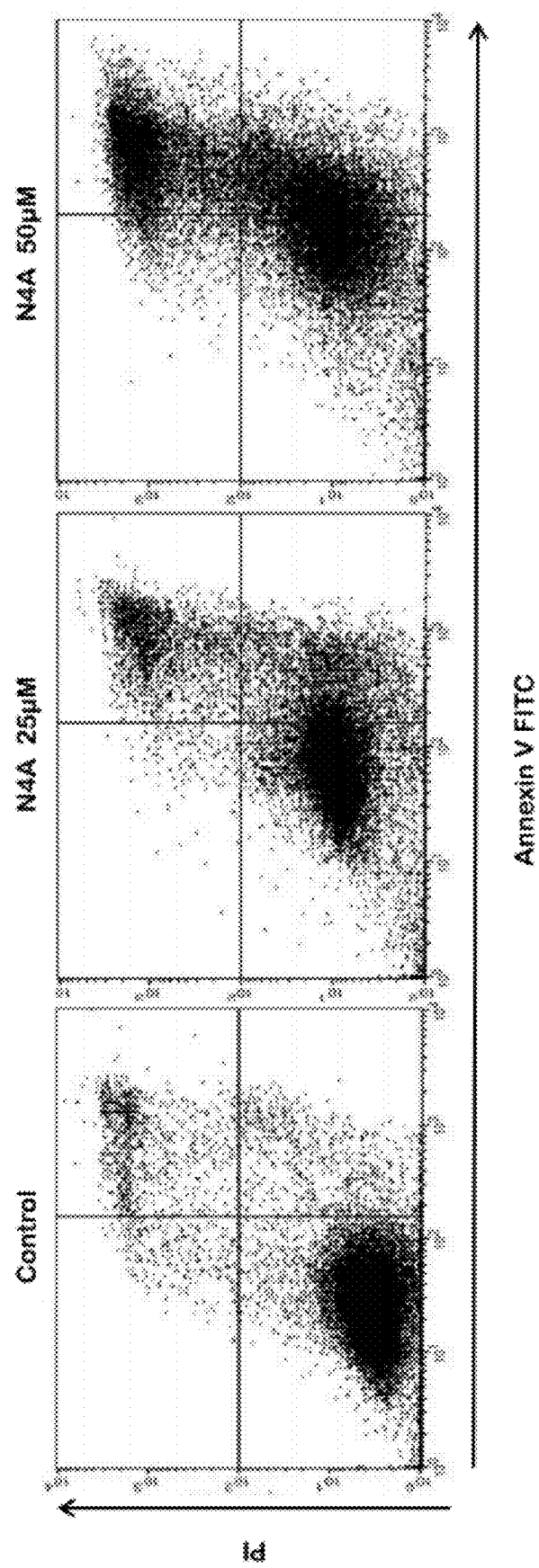
FIGS. 8A-8D show the induction of cell death in HeLa cells by the PFKFB3 inhibitors, N4A and YN1. The cells were treated with two different concentrations of each of the inhibitors, 25 µM and 50 µM.
Figure 8B:
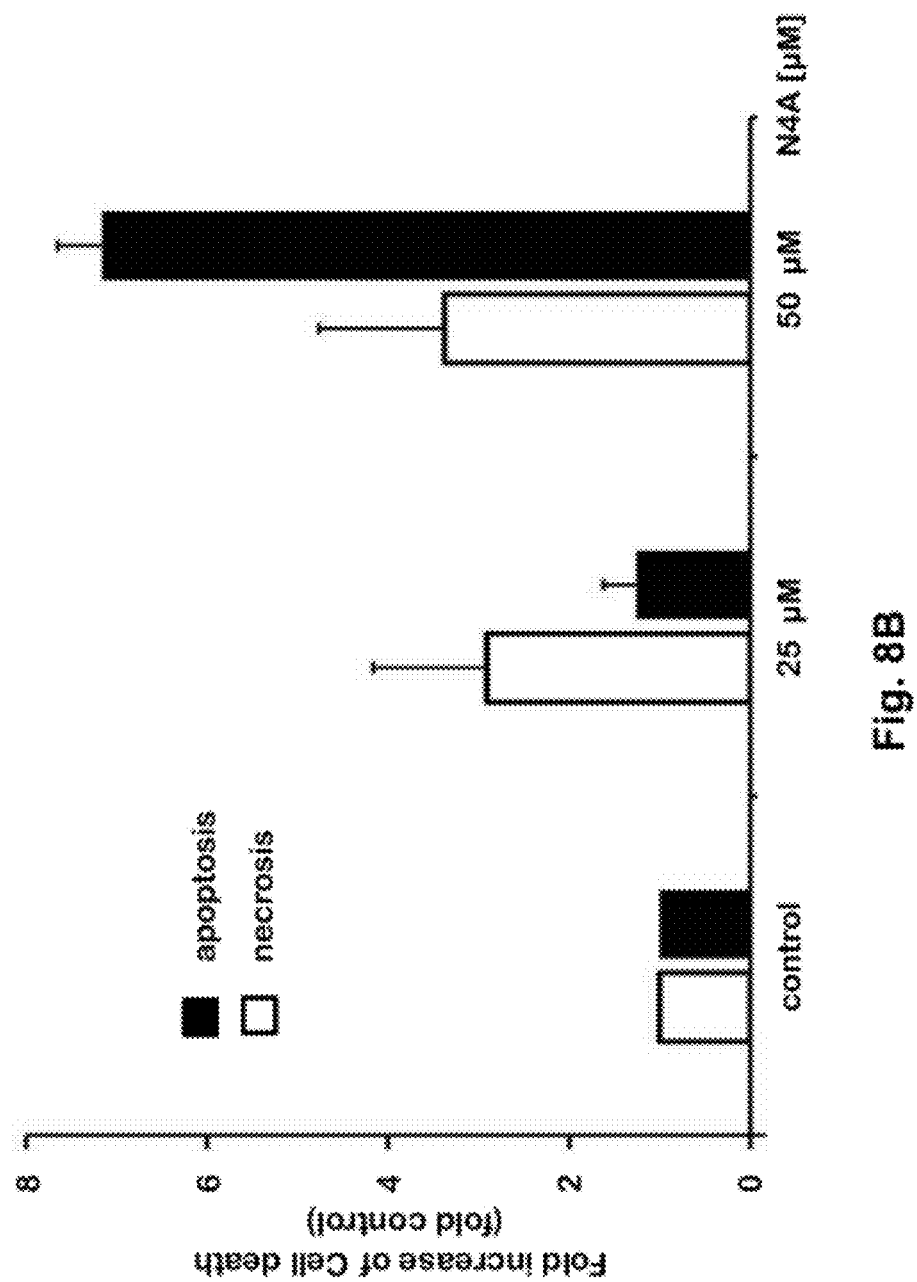
Figure 8C:
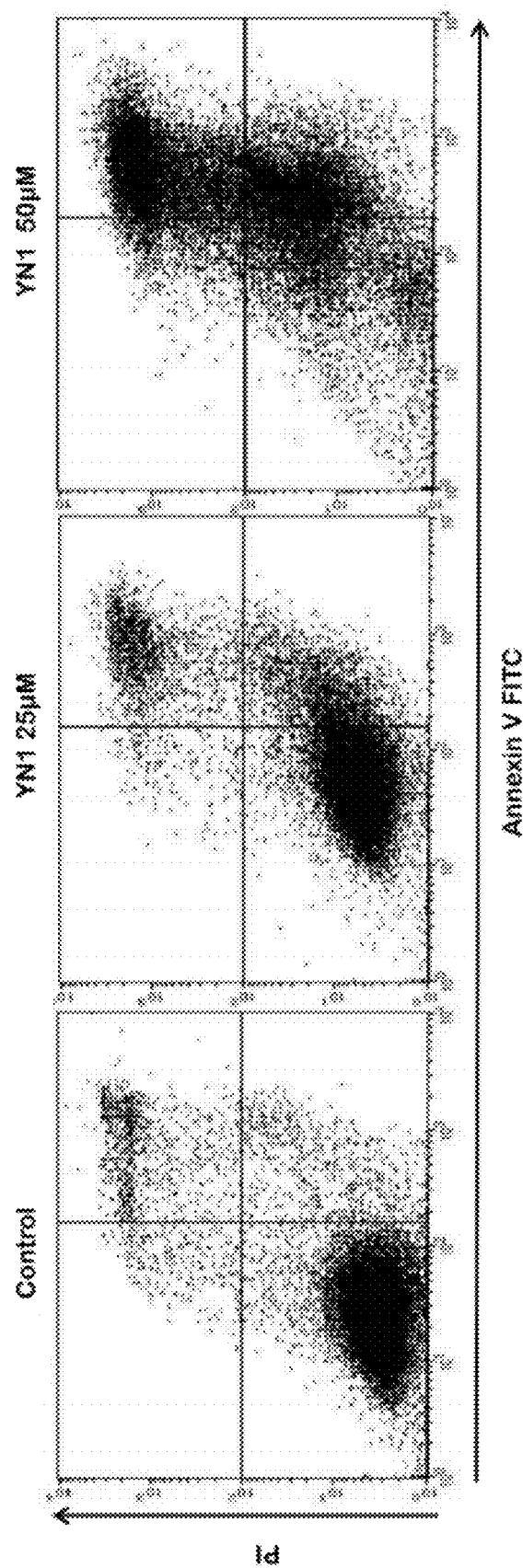
Figure 8D:
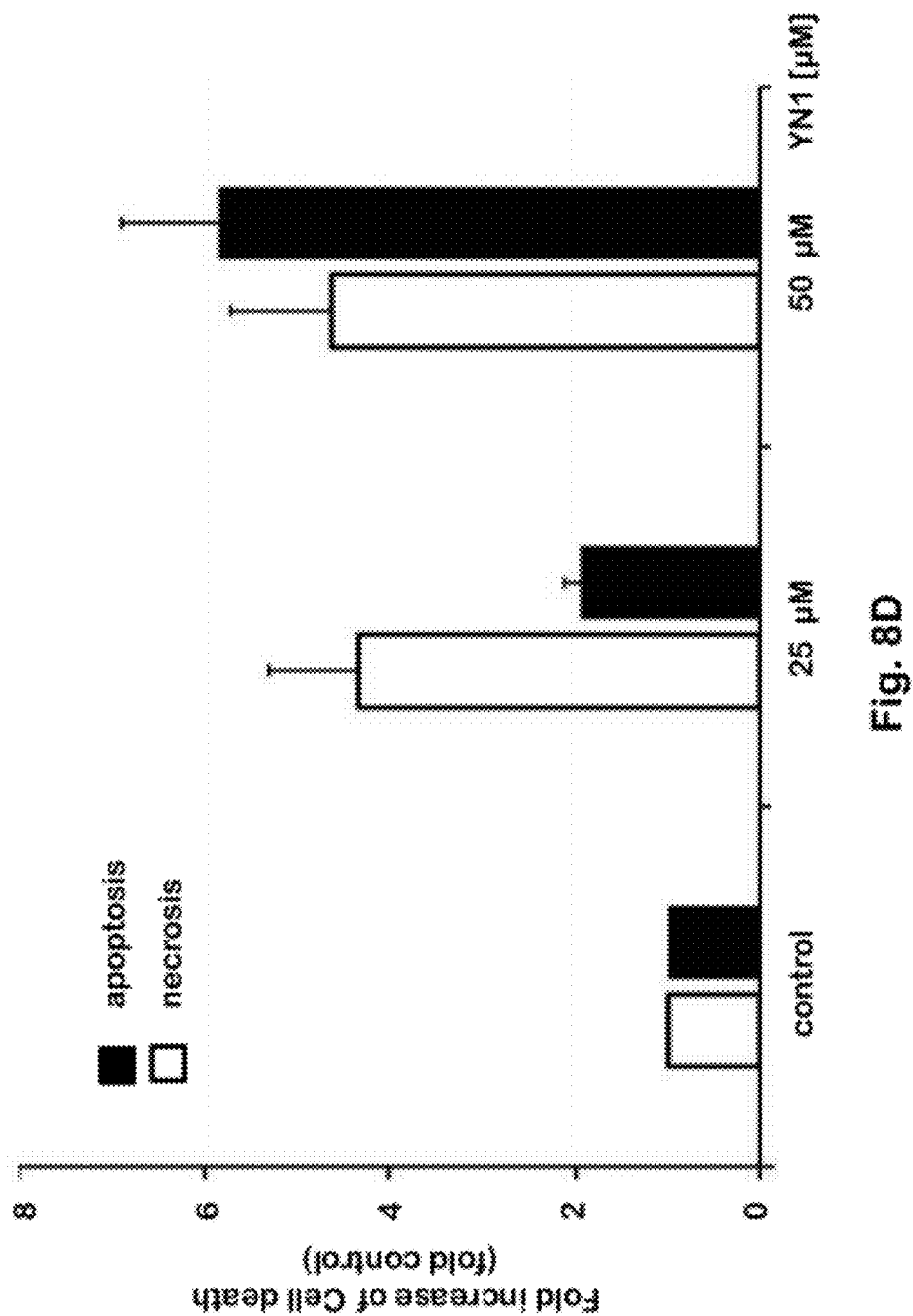

N4A and YN1 were also able to inhibit soft agar colony formation in HeLa cells (FIGS. 7A-7B). HeLa cells were plated in soft agar with different concentrations of N4A or YN1 and grown for 3 weeks to allow colony formation. Both compounds significantly inhibited colony formation at 25, 50 and 100 µM. Colony formation was inhibited by 64% and 79% in the presence of 25 µM N4A and YN1, respectively.

To further investigate the mechanism responsible for the anti-proliferative effect of the PFKFB3 inhibitors, a flow-cytometric analysis of cell death was performed. The results indicated that N4A and YN1 induced both apoptotic and necrotic cell death as shown in FIGS. 8A-8D. This mixed pattern is related to the nature of apoptosis, which, unlike necrosis, is an ATP-dependent process [60, 61]. Without being bound by theory, it was expected that that cell death induced by the PFKFB3 inhibitors should correlate with their ability to deplete cellular ATP and depletion of ATP favors death by necrosis as previously speculated [44, 60, 61]. The present data supports this interpretation: at a relatively low concentration (25 µM) of N4A or YN1, an environment in which depletion of cellular energy depletion is moderate, cells were found to be prone to apoptosis, whereas, at higher concentrations (50 µM) of inhibitors, death by necrosis was significantly increased due to insufficient cellular energy to support the apoptotic process (FIGS. 8A-8D).

Example 5

Structural Analysis of the PFKFB3.N4A Complex

The N4A inhibitor was used as a "lead" compound for structure-guided optimization of further inhibitors. To facilitate this task, it was necessary to determine the molecular characteristics of N4A binding to PFKFB3 by crystallizing human PFKFB3 in the presence of N4A. Accordingly, the structure of this complex was determined to 2.4 Å resolution by a method of molecular replacement using the first PFKFB3 structure (PDB code: 2AXN) as a search model [62]. An |Fo|-|Fc| omit map enabled unambiguous placement of N4A into the Fru-6-P binding pocket of the kinase domain of PFKFB3. The N4A located at the Fru-6-P pocket could be superimposed onto the Fru-6-P modeled in the structure of PFKFB3 in a ternary complex with AMPPCP and Fru-6-P (PDB code: 2DWP) [62].

This structure provided clear evidence, supporting the kinetic observations that N4A competes with Fru-6-P for the same binding pocket in PFKFB3. Modeling indicates that N4A is anchored to the Fru-6-P pocket via hydrogen bonds with Arg74, Asp124, Thr126, and Arg132. The phenol moiety of N4A is unfavorably located in the pocket where the 6-phosphate moiety of Fru-6-P interacts through a hydrogen bond with Arg132 and results in Arg132 adopting a different conformation in the N4A complex. The chromone moiety of N4A occupies the same position as the fructose moiety. Here, two of N4A's hydroxyl groups mimic the hydrogen-bonding pattern of the hydroxyl groups at the C3 and C4 positions of the fructose moiety. The binding competence of N4A is further strengthened by a number of water-mediated hydrogen bonds between the hydroxyl group of the N4A with Thr48, Arg98, Asp124, Thr126, and Tyr193 and the conformational changes induced upon the binding. The protein ligand interactions are summarized in Table 2.

TABLE 2

Interactions between inhibitors and PFKFB3

| Protein residue | Water | Inhibitor N4A | Type of interaction | Distance (Å) |
|---|---|---|---|---|
| Arg74 | NE | O4 | Hydrogen bond | 2.9 |
| | NH2 | O5 | Hydrogen bond | 3.0 |
| Asp124 | O | O8 | Hydrogen bond | 3.5 |
| Thr126 | OG1 | O1 | Hydrogen bond | 3.3 |
| Arg132 | NE | O4' | Hydrogen bond | 2.2 |
| Arg98 | | Phenol moiety | Cation-π interaction | 5 |
| Thr48 | OG1 | HOH38 | | 3.3 |
| Asp124 | OD1 | HOH38 | | 3.2 |
| | | HOH38 O7 | Water mediated interaction | 2.3 |
| Thr126 | OG1 | HOH97 | | 3.5 |
| Tyr193 | OH | HOH97 | | 2.2 |
| | | HOH97 O1 | Water mediated interaction | 2.6 |

| Protein residue | Water | Inhibitor YN1 | Type of interaction | Distance (Å) |
|---|---|---|---|---|
| Arg75 | NH1 | O4' | Hydrogen bond | 3.5 |
| Arg98 | NE | O8 | Hydrogen bond | 3.2 |
| Thr126 | OG1 | O4 | Hydrogen bond | 3.5 |
| Arg98 | | Chromone moiety | Cation-π interaction | 4 |
| Arg189 | | Phenol moiety | Cation-π interaction | 3.5 |

When compared with PFKFB3 that is complexed with AMPPCP and Fru-6-P (PDB code:2DWP), the N4A-PFKFB3 complex induced no significant difference in global structure. However, the differences around the F-6-P binding pocket were evident from 3D modeling (data not shown). Upon N4A binding, the Arg132 side chain swings out about 3.5 Å from the position for Fru-6-P site, offering space to accommodate N4A. As a consequence, Glu131 in the same helix moves toward the F-6-P pocket by ~2 Å. The guanidino group of Arg75 moved 1.5 Å toward the inhibitor from its original position, implying that the closer positioning of Arg75 stabilizes inhibitor binding. The phenol group on Tyr424 is tilted toward N4A due to the repositioning of water molecules near Tyr424 upon N4A binding. These local conformational changes in the F-6-P pocket affect the mobile ATP loop, especially a turn (residues 168-180), which flips into the F-6-P pocket, a displacement of over 2 Å (data not shown).

Compounds YN1 and YZ9 Derived from Evaluation of N4A Scaffold

Compound YN1:

To increase the inhibition potency of N4A, a similarity search using N4A as a template and with a defined Tanimoto coefficient ≥0.9 [63] was performed. The selected molecules from the entire NCI Database were evaluated via computational docking [59] and, as a result, ZINC06093399 (YN1) was selected as predicted to have significantly improved potency as a PFKFB3 inhibitor. YN1, purchased from CHESS GmbH, was tested for its inhibition potency and kinetic properties and demonstrated a 5-fold increase in PFKFB3 inhibition compared to N4A (Table 1). The structure of YN1 is shown in FIG. 5B.

In order to determine the molecular basis for the increased inhibition potency of YN1, the crystal structure of the PFKFB3 in complex with YN1 was determined at a resolution of 3.3 Å. Because of this resolution limit, the structure refinement was performed using only rigid body and B-group refinement, taking the whole protein structure of the N4A complex as a rigid body.

Similar to N4A, YN1 binds to the Fru-6-P binding pocket shown in an omit |Fo|−|Fc| electron density map data (data not shown). In addition, like N4A, YN1 interacts with PFKFB3 by occupying the Fru-6-P pocket. However, the electron density for YN1 was better modeled by flipping YN1 180° in respect to its short axis, compared to the orientation of N4A, resulting in the phenol moiety of YN1 being positioned towards the site occupied by the fructose moiety of Fru-6-P rather than the site of the phosphate of Fru-6-P. This orientation may be a consequence of the substitution of benzenediol for benzenetetrol in the chromone moiety of the two inhibitors. Without wishing to be bound by this theory, the additional hydroxyl groups on the chromone moiety of N4A perhaps cannot be accommodated at the binding site for the 6-phosphate moiety of Fru-6-P. However, YN1 with a loss of two hydroxyl groups in the same chromone moiety was able to bind to the site in a direction opposite that of N4A. The chromone moiety of YN1 is inserted between Val70 and Phe87 gaining hydrophobic interactions and a Cation-π interaction with Arg98, while its phenol moiety gains a Cation-π interaction with Arg189 and a hydrogen bond with Arg75 (Table 2). Water mediated interactions, similar to those observed in the N4A complex, very likely contribute to the YN1 interaction, although the resolution limit did not allow for the modeling of water in the YN1 complex.

The present observations regarding YN1 can be supported by evidence from high resolution X-ray data. Nevertheless, because only the position of YN1 was refined inside the N4A binding pocket as a rigid body, this new binding mode observed for YN1 is significant. Comparison of the binding modes of N4A and YN1 suggested that the Fru-6-P pocket of PFKFB3, with a number of Arg residues present, is surprisingly generous to the binding of compounds with hydrophobic rings. It is likely that the pocket takes advantage of Cation-π interactions as seen in other structures [64] and water-mediated hydrogen bonds. The higher potency of YN1 compared to N4A and the apparent difference in binding modes between the two compounds, taken together, suggest that compounds containing a chromone moiety with fewer hydroxyl groups will be more potent than either N4A or YN1.

Compound YZ9:

Using a strategy similar to that used to find YN1, the molecule designated YZ9 was also identified. Using the same biological test routine, we determined that YZ9 inhibited PFKFB3 with an IC50 of 0.183 μM, and acted as a competitive inhibitor against Fru-6-P with a Ki of 0.094 μM (Table 1). YZ9 also inhibited the cell growth with a GI50 of 2.7 μM. The structure of YZ9 is shown in FIG. 5B.

For Examples 2-5, Materials and Methods were as follows:

2-Kase Assay and Kinetic Analysis:

To determine steady-state initial reaction rates, the 2-Kase reactions were performed first and the Fru-2,6-BP produced was measured by a conventional enzyme-coupled kinetics assay as described previously[62, 69]. The compounds, N4A and RBC2 came from the National Cancer Institute as indicated in Example 1. The compound YN1 (7,8-dihydroxy-3-(4-hydroxyphenyl)chromen-4-one) was purchased from INDOFINE Chemical (Hillsborough, N.J.); and the compound YZ9 (ethyl 7-hydroxy-2-oxochromene-3-carboxylate) was purchased from TimTec (Newark, Del.). Initial rates of decrease in absorbance (Abs) at 340 nm were corrected with the rate of the control reaction in which no Fru-2,6-BP was present. Negative controls were carried out in the absence of enzyme and positive controls indicate the reaction in the presence of enzyme without inhibitor compounds. The percentage of Inhibitory activity was calculated according to the formula: % inhibition=100×[1−(Abs$_{negative\ control}$−Abs$_{compound}$)/(Abs$_{negative\ control}$−Abs$_{positive\ control}$)]. IC$_{50}$ values were determined in quadruplicate. For the kinetic studies, concentrations of one of substrate and inhibitor were varied, and decrease in absorbance at 340 nm was measured. The inhibition patterns were analyzed using the program written by Cleland, in which Ki is the dissociation constants for the inhibitor from enzyme-inhibitor complex [70]. For Selectivity studies, the 2-Kase assays were performed first and the F-2,6-P2 produced was measured by an enzyme coupled kinetics assay as described above. The His6-tagged PFKFB isoforms, PFKFB1, PFKFB2, and PFKFB4 were expressed in *Escherichia coli* C41(DE3) and purified using Ni-NTA affinity columns.

Similarity Search:

Similarity searches, using e.g. N4A or YN1 as a template, were performed using the NCI Enhanced Web Browser (http://129.43.27.140/ncidb2/) with a defined Tanimoto coefficient ≥0.9 [63]. The entire Open NCI Database was used using Tanimoto index, and the selected compounds were consequently evaluated through docking. Docking was performed on the structure of the PFKFB3.ADP.F6P complex (PDB code: 2AXN), using FlexX, after stripping the ligands [59, 62]. The docking calculations were performed with an active-site encompassing a sphere of 15 Å around the reference structure position in the PDB file. The high rank compounds were primarily purchased from CHESS GmbH (Germany) or from other commercial suppliers.

Preparation and Crystallization of PFKFB3:

Preparation of the protein sample and its crystallization was performed as previously described [58]. The 6×His-tagged human PFKFB3 was expressed in *Escherichia coli* BL21(DE3) pLysS and purified using Ni-NTA affinity columns and, subsequently, Mono Q anion-exchange chromatography. The resulting pure protein was kept, after concentrating to 8 mg ml$^{-1}$ protein, in 20 mM Tris.HCl (pH 8.0), 10 mM NaP$_i$, 0.05 mM EDTA, 5 mM β-mercaptoethanol, 5% glycerol, 0.2 mM Fru-6-P. Crystals were prepared by the sitting-drop, vapor-diffusion method with a 1:1 (v/v) mixture of the protein sample with a reservoir solution of 50 mM HEPES pH 7, 7-20% DMSO, 0.2-1.5 mM of inhibitors, and 7% (w/v) polyethylene glycol 4000. Crystals with a size of 0.2 mm×0.1 mm×0.2 mm grew in two to three weeks.

Cell Culture:

HeLa and T47D cell lines were cultured in a 10% $CO_2$ humidified atmosphere at 37° C. as exponentially growing monolayers in Dulbecco's modified Eagle's medium (DMEM) with glutamax (Invitrogen), supplemented with 10% fetal calf serum (Invitrogen) and penicillin/streptomycin (100 U/ml and 100 μg/ml). The human cervical carcinoma cell line, HeLa, was kindly provided by Dr. J. Kim (Louisiana State University) and the human breast carcinoma cell line, T47D, was obtained from the American Type Culture Collection (Manassas, Va.).

Metabolite Determination:

HeLa cells were plated at a density of $2.5 \times 10^5$ in a 6-well plate in DMEM containing 10% FCS. The media were replaced with fresh DMEM containing either vehicle (dimethyl sulfoxide) or 25 μM of inhibitor the following day. After 0, 4, 8, 12, 24, or 48 hours of incubation with each inhibitor, media samples were collected for measuring the lactate secretion levels using a lactate oxidase-based assay kit (Sigma-Aldrich), and the lactate concentration was normalized to the total cellular protein concentration. The Fru-2,6-BP level was determined with collected cells at times of 0, 4, 8, 12, 24, or 48 hours after the treatment, using the method described previously [69].

Cell Proliferation/Survival Assays:

Cell growth inhibition was determined by an XTT-based in-vitro toxicology assay (Sigma-Aldrich) or trypan blue staining. Cells were plated at a density of $3.5 \times 10^4$ per well in a 24-well plate in DMEM containing 10% FCS. These cells were allowed to attach for 24 hours, and the media were replaced with fresh media containing either vehicle (dimethyl sulfoxide) or appropriate concentrations of test compounds. After 36 hours of incubation with either vehicle or compounds, cells were trypsinized and cell viability was determined by the trypan blue exclusion assay using a hemacytometer. For the XTT assay, cells were seeded into 96-well cell culture plates at a density of $0.6 \times 10^4$ per well. After the appropriate treatment described above, cells were incubated with 0.1 mg/ml of 2,3-bis(2-methoxy-4-nitro-5-sulfophenyl)-5-[(phenylamino)carbonyl]-2H-tetrazolium hydroxide (XTT) for 4 hours, and then cell number was determined by the absorbance at 470 nm, which is proportional to the number of cells that remained attached to the plate. $GI_{50}$s were calculated as the inhibitor concentration needed for 50% of vehicle-treated cell growth. The appearance of apoptotic or necrotic cells was determined by flow cytometric analysis of cells double stained with Annexin V-FITC and propidium iodide (PI) [71]. Apoptotic and necrotic cells were distinguished on the basis of double-labeling for Annexin V-FITC (Sigma-Aldrich) and PI, a membrane-impermeable DNA stain. Floating and freshly trypsinized cells were pooled, washed twice in binding buffer, and processed following manufacturer's instructions. The fluorescence of samples were analyzed by flow cytometry (FACSCalibur®, Becton Dickinson Immunocytometry, San Jose, Calif.) using the CellQuest (BD Bioscience, Immunocytometry Systems, San Jose, Calif., USA) software.

HeLa cell colony formation was determined by soft agar assay. Cells ($2 \times 10^3$) were mixed in DMEM medium containing 0.35% agarose and varying concentrations of N4A or YN1. Then the cell mixture was added on a layer of 0.6% concentration of bottom agar in 24 well plate and allowed to grow for three weeks at 37° C. under 5% $CO_2$. Fresh medium containing the inhibitors or vehicle (DMSO) was changed every four days. Colonies of 50 cells or more were counted after three weeks. The experiments were repeated at least five times.

Diffraction Data Collection and Processing:

Crystals were soaked with cryoprotectant solutions for 0.5 to 2 hours before cryogenic data collections. Depending on the experimental aims, cryoprotectant solutions (a crystallization reservoir solution enriched with 30% glycerol) were enriched with 0.3 mM of inhibitor. A soaked crystal was flash-frozen at 100 K using an Oxford cryo-device and kept at the same temperature during data collections. The diffraction data were collected at The Northeastern Collaborative Access Team (NE-CAT) Beamline at the Advanced Photon Source, Argonne National Laboratory, Argonne, Ill. The X-ray source wavelength was 0.9792 Å. The data recorded on a ADSC Q315 detector were integrated, merged, and scaled using XDS as described previously [72]. Statistics of the diffraction data and structure refinement are summarized in Table 1. The crystals belong to $P6_522$ space group with similar cell dimensions.

Structure Determination and Refinement:

The reduced data were formatted for the program suites of CCP4 [73], and 10% of the data were marked for free R-factor measurements in subsequent structure refinements. The search model was built from the coordinates of the PFKFB3.Fru-6-P.EDTA complex structure (PDB accession code 2AXN) [73] by stripping all the included ligand and solvent molecules to determine the N4A complex structures of PFKFB3. The initial model was determined using REFMAC within the CCP4 suit and processed through iterated cycles of manual model rebuilding and validation using the program COOT [73]. Binding of the ligands was confirmed, referring to the |Fo|–|Fc| omit maps that were generated, when $R_{crys}/R_{free}$ reached 0.23/0.29 or below. Referring to these maps, Fru-6-P, N4A or YN1 was incorporated into the corresponding complex models.

As summarized in Table 3, the final model of the PFKFB3.Fru-6-P.N4A complex has Rcrys/Rfree of 0.215/0.262 using a total of 3881 scatterers, including solvent molecules, against all available 26,883 reflections in the resolution range of 61.6-2.4 Å. The structure contains a total of 443 amino acid residues of the full-length protein of 520 residues. As in the PFKFB3.ADP.EDTA complex, the C terminus (residues 446-520) is mostly disordered.

The PFKFB3.Fru-6-P.YN1 complex was built from N4A complex through only rigid body and B-group refinement because of resolution limit, resulting with $R_{free}/R_{crys}$ of 0.243/0.250 using a total of 3700 scatterers against all available 12,140 reflections in the resolution range of 89.0-3.3 Å. The structure contains a total of 448 amino acid residues of the full length protein of 520 residues. In the both structures, more than 89% of the residues are in the most favored region, 9.5% in the additional region, and the rest in the generously allowed region in the Ramachandran plots. The structure refinement statistics are summarized in Table 3.

TABLE 3

Statistics of reflection data and structure refinements

| | PFKFB3•Fru-6-P•N4A | PFKFB3•Fru-6-P•YN1 |
|---|---|---|
| Space group | $P6_522$ | $P6_522$ |
| Unit cell dimensions | | |
| a = b (Å) | 101.70 | 102.78 |
| c (Å) | 258.61 | 260.10 |
| Resolution range (Å) | 61.6-2.4 | 50.4-3.3 |

TABLE 3-continued

Statistics of reflection data and structure refinements

| | PFKFB3•Fru-6-P•N4A | PFKFB3•Fru-6-P•YN1 |
|---|---|---|
| No. reflections used | 26,883 | 20,476 |
| Completeness (%) | 100.00 | 88.96 |
| Redundancy | 7.2 (2.6) | 9.5 (2.2) |
| I/σ (I) | 10.03 | 6.2 |
| $R_{sym}$ | 0.055 | 0.069 |
| $R_{crys}$ | 0.215 | 0.243 |
| $R_{free}$ | 0.262 | 0.250 |
| No. amino acids | 443 | 441 |
| No. protein atoms | 3881 | 3637 |
| No. hetero atoms | 52 | 40 |
| No. water molecules | 192 | — |
| r.m.s.d. from ideal | | |
| Bond lengths (Å) | 0.021 | — |
| Bond angles (deg.) | 2.016 | — |
| Dihedral angles (deg.) | 20.9 | — |
| Mean Bfactor | | |
| Protein atoms (Å$^2$) | 35.53 | 90.93 |
| Hetero atoms (Å$^2$) | 48.23 | 106.73 |
| Water atoms (Å$^2$) | 43.08 | — |

$R_{sym} = \Sigma_h(\Sigma_j|I_{h, j} - <I_h>|/\Sigma_{j_{h, j}})$, where h = set of Miller indices, j = set of observations of reflection h, and $<I_h>$ = the mean intensity. $R_{crys} = \Sigma_h||F_{o, h}| - |F_{c, h}||/\Sigma_h|F_{o, h}|$. $R_{free}$ was calculated using 10% of the complete data set excluded from refinement. The numbers in parentheses represent values from the highest resolution shell.

Example 6

Embodiments of Inhibitory Molecules

As noted above, phosphofructokinase is an important control point in the glycolytic pathway, since it involves one of the irreversible steps. In the glycolysis pathway, phosphofructokinase-1 (PFK-1) catalyzes the major rate-limiting step that converts fructose-6-phosphate (Fru-6-P) to fructose-1,6-bisphosphate (Fru-1,6-BP). PFK-1 is allosterically regulated by fructose-2,6-bisphosphate (Fru-2,6-BP). Fru-2,6-BP is the most potent glycolysis stimulator.

The 6-phosphofructo-2-kinase/fructose-2,6-bisphosphatases (PFKFB) family of bifunctional enzymes is responsible for increasing intracellular levels of Fru-2,6-BP. There are four known PFKFB isozymes, PFKFB1, PFKFB2, PFKFB3, and PFKFB4. Among these isozymes, PFKFB3 has been found to be overexpressed in numerous tumor cell lines. In addition, studies have shown that induction of PFKFB3 expression by HIF-1 under hypoxic conditions is followed by increased invasive potential and enhanced resistance to chemotherapies.

This example and the Tables 4-9 set forth embodiments of inhibitory molecules in accordance with the present invention. These molecules are used in methods to affect mammalian energy metabolism, such as by inhibiting one of the 6-phosphofructo-2-kinase/fructose-2,6-bisphosphatases (PFKFBs) involved in glycolysis. In a particular embodiment, these molecules are used as inhibitors of the isozyme PFKFB3, and for cancer therapy.

Accordingly, the molecules set forth in Tables 4-9 are used to affect or modulate glycolytic energy metabolism. The molecules set forth in Tables 4-9 are used to inhibit at least one of PFKFB1, PFKFB2, PFKFB3, or PFKFB4, and preferentially inhibitor to inhibit isozyme PFKFB3 relative to the other PFKFB isozymes. The molecules set forth in Tables 4-9 are used therapeutically on a cell, cells, tissue, or organ that is preferentially dependent on glycolytic metabolism that has heightened or upregulated glycolytic metabolism, for example cancer tissues.

Tables 4 and 5

As set forth in Table 4, a molecule of the invention is specified by the formula:

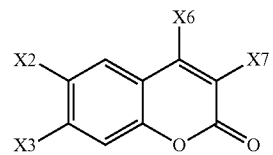

wherein:
X2 and X3 are independently selected from the group consisting of —H, —OH, and halogen; and X2 and X3 may be the same or different;
X6 is —H or —CH$_3$;
X7 is —C(O)OR; and
R is selected from the group consisting of H, C$_1$ to C$_5$ alkyl, C$_1$ to C$_5$ alkenyl, and C$_2$ to C$_4$ alkaneamide.

(Note, the substituent groups are uniquely defined for each respective pair of Tables 4 and 5; Tables 6 and 7; and Tables 8 and 9.)

Selected embodiments of molecules in accordance with the formula of Table 4 are set forth in Table 5.

One embodiment in accordance with the formulae of Table 4 is the molecule ethyl 7-hydroxy-2-oxochromene-3-carboxylate, (referred to herein as YZ9):

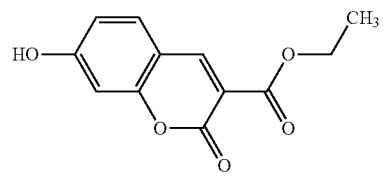 [SMILES: CCOC(=O)c1cc2ccc(O)cc2oc1=O]

Tables 6 and 7

As set forth in Table 6, a molecule of the invention is specified by the formula:

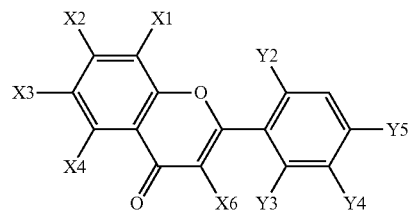

wherein:
X1, X2, X3, X4, X6, Y2, Y3, and Y4 are each independently selected from the group consisting of —H and —OH; and the several substituents X1, X2, X3, X4, X6, Y2, Y3, and Y4 may be the same as or different from one another; and
Y5 is selected from the group consisting of —H, —OH, and —OCH$_3$.

Selected embodiments of molecules in accordance with the template formula of Table 6 are set forth in Table 7.

One embodiment in accordance with the formula of Table 6 is 5,6,7,8-tetrahydroxy-2-(4-hydroxyphenyl)chromene-4-one (also referred to herein by the names N4A or NSC76988):

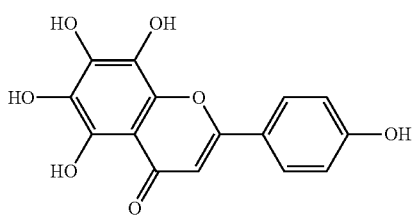 [SMILES: O=c1cc(-c2ccc(O)cc2)oc2c(O)c(O)c(O)c(O)c12]

Another embodiment in accordance with the formula of Table 6 is 7,8-dihydroxy-3-(4-hydroxyphenyl)chromen-4-one (also referred to herein as YN1):

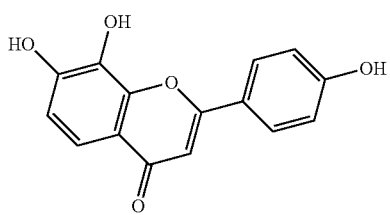 [SMILES: O=c1cc(-c2ccc(O)cc2)oc2c(O)c(O)ccc12]

Tables 8 and 9

As set forth in Table 8, a molecule of the invention is specified by the formula:

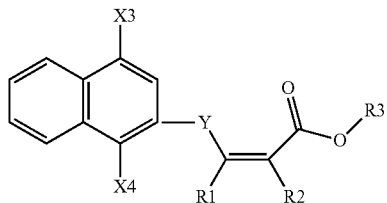

wherein:

X3 and X4 are independently selected from the group consisting of —H, and —OH; and X3 and X4 may be the same or different;

Y is —S— or

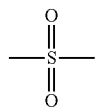

R1 and R2 are independently selected from the group consisting of —H, and —CH$_3$; and R1 and R2 may be the same or different;

R3 is —CH$_3$ or —CH$_2$CH$_3$; and the configuration at the carbon-carbon double bond in the X2 group is either cis or trans (E or Z).

Selected embodiments of molecules in accordance with the template formula of Table 8 are set forth in Table 9.

One embodiment in accordance with the formula of Table 8 is (Z)-ethyl 3-((1,4-dihydroxynaphthalen-2-yl)thio)but-2-enoate (also referred to herein as RBC2 or NSC278631):

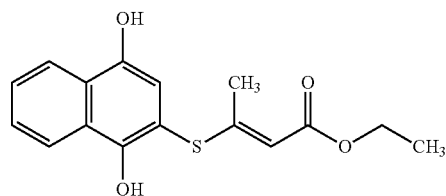 [SMILES: CCOC(=O)/C=C(\C)Sc1cc(O)c2ccccc2c1O]

TABLE 4

Compound Group I (YZ9 Group): Template and Exemplary R Groups

| Template | Representative Compound Tested |
|---|---|
| X1 = R1<br>X2 = R1, R2, R3, or R4<br>X3 = R1, R2<br>X6 = R1 or R5<br>X7 = R6, R7, R8, R9, R10, R11, R12, R13, R14, or R15 | ethyl 7-hydroxy-2-oxochromene-3-carboxylate<br>(named, YZ9) |

| Exemplary R groups. | | | |
|---|---|---|---|
| R1 | —H | R2 | —OH |
| R3 | —Br | R4 | —Cl |
| R5 | —CH$_3$ | R6 | (ethyl ester group) |

TABLE 4-continued
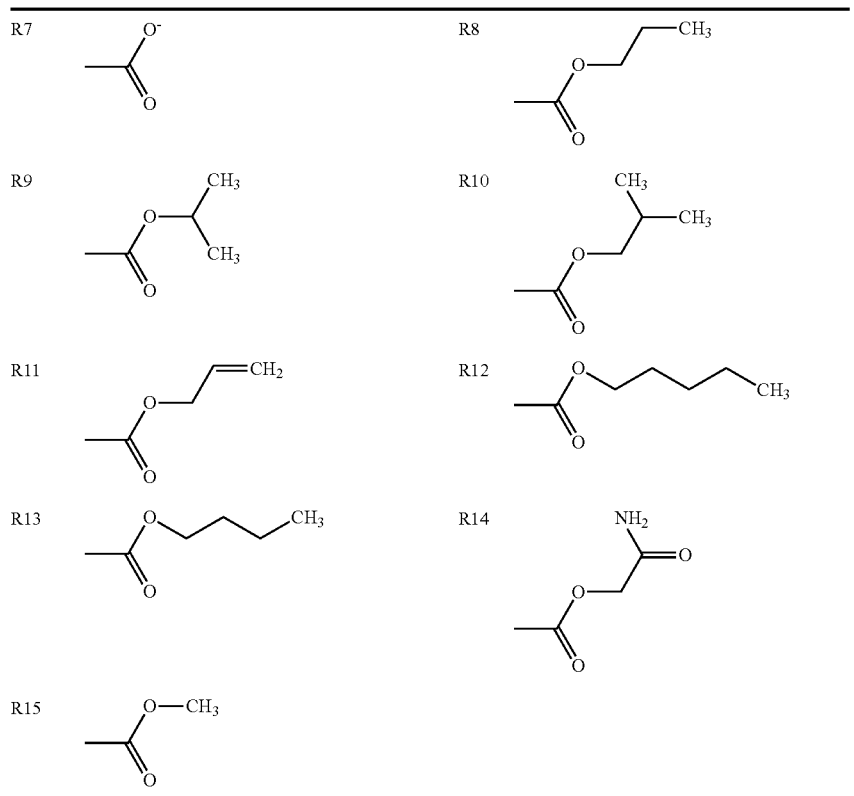
TABLE 5
Compound Group I: Exemplary Derivatives of YZ9
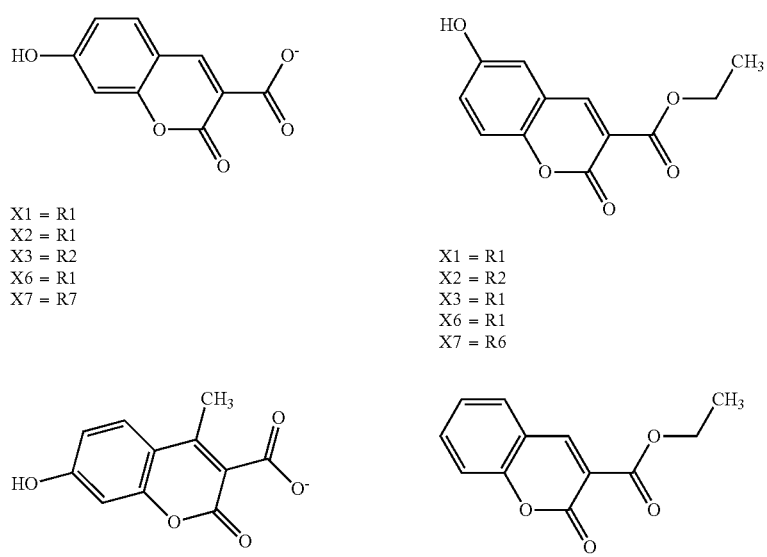

TABLE 5-continued
Compound Group I: Exemplary Derivatives of YZ9
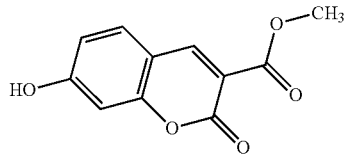 [SMILES: COC(=O)c1cc2ccc(O)cc2oc1=O]
X1 = R1
X2 = R1
X3 = R2
X6 = R1
X7 = R15
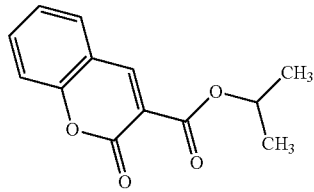 [SMILES: CC(C)OC(=O)c1cc2ccccc2oc1=O]
X1 = R1
X2 = R1
X3 = R1
X6 = R1
X7 = R9
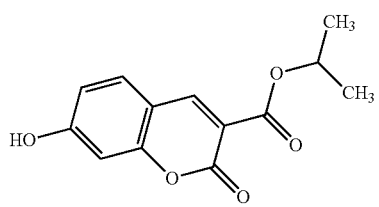 [SMILES: CC(C)OC(=O)c1cc2ccc(O)cc2oc1=O]
X1 = R1
X2 = R1
X3 = R2
X6 = R1
X7 = R9
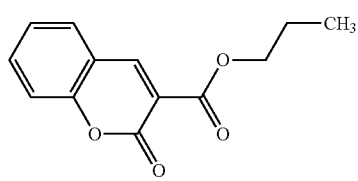 [SMILES: CCCOC(=O)c1cc2ccccc2oc1=O]
X1 = R1
X2 = R1
X3 = R1
X6 = R1
X7 = R8
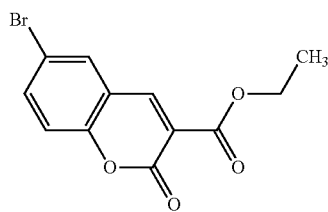
X1 = R1
X2 = R3
X3 = R1
X6 = R1
X7 = R6
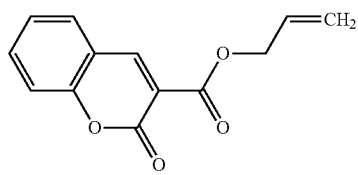 [SMILES: C=CCOC(=O)c1cc2ccccc2oc1=O]
X1 = R1
X2 = R1
X3 = R1
X6 = R1
X7 = R11
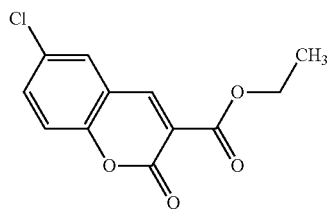 [SMILES: CCOC(=O)c1cc2cc(Cl)ccc2oc1=O]
X1 = R1
X2 = R4
X3 = R1
X6 = R1
X7 = R6
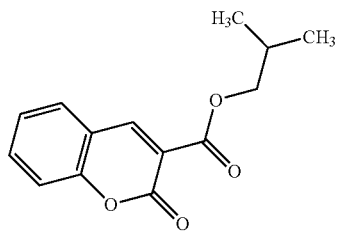 [SMILES: CC(C)COC(=O)c1cc2ccccc2oc1=O]
X1 = R1
X2 = R1
X3 = R1
X6 = R1
X7 = R10

TABLE 5-continued

Compound Group I: Exemplary Derivatives of YZ9

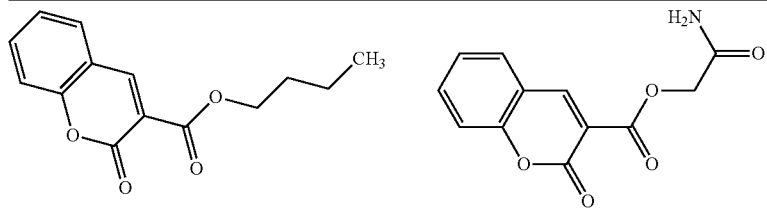

X1 = R1
X2 = R1
X3 = R1
X6 = R1
X7 = R13

X1 = R1
X2 = R1
X3 = R1
X6 = R1
X7 = R14

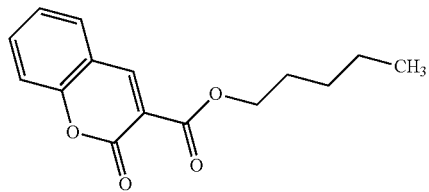 [SMILES: CCCCCOC(=O)c1cc2ccccc2oc1=O]

X1 = R1
X2 = R1
X3 = R1
X6 = R1
X7 = R12

TABLE 6

Compound Group II (N4A and YN1 Group): Templates and Exemplary R groups

| Template | Exemplary R groups | |
|---|---|---|
| 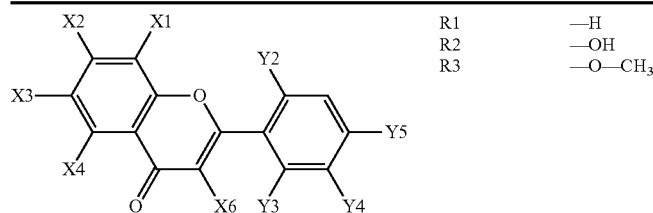 | R1 | —H |
| | R2 | —OH |
| | R3 | —O—CH$_3$ |

X1 = R1 or R2
X2 = R1 or R2
X3 = R1 or R2
X4 = R1 or R2
X6 = R1 or R2
Y2 = R1 or R2
Y3 = R1 or R2
Y4 = R1 or R2
Y5 = R1, R2, or R3

Representative compounds tested

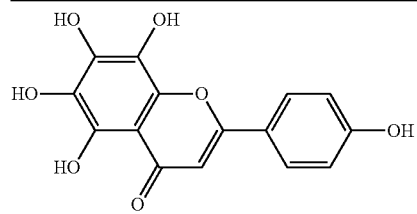

5,6,7,8-tetrahydroxy-2-(4-hydroxyphenyl)chromene-4-one
N4A, NSC76988

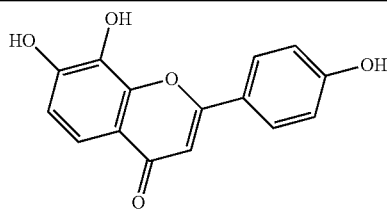

7,8-dihydroxy-3-(4-hydroxyphenyl)chromen-4-one
YN1

TABLE 7
Compound Group II: Exemplary Derivatives of N4A and YN1
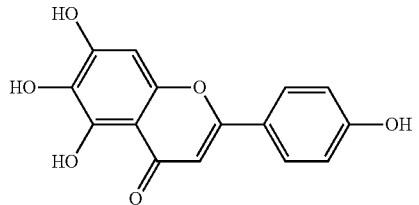 [SMILES: O=c1cc(-c2ccc(O)cc2)oc2cc(O)c(O)c(O)c12]
X1 = R1
X2 = R2
X3 = R2
X4 = R2
X6 = R1
Y2 = R1
Y3 = R1
Y4 = R2
Y5 = R1
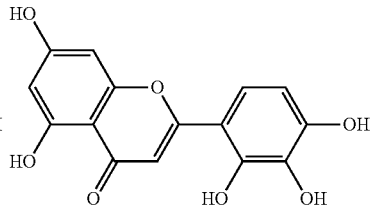
X1 = R1
X2 = R2
X3 = R1
X4 = R2
X6 = R1
Y2 = R1
Y3 = R2
Y4 = R2
Y5 = R1
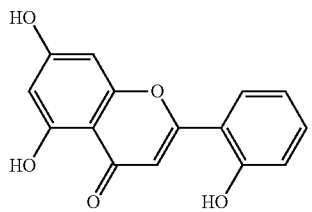 [SMILES: O=c1cc(-c2ccccc2O)oc2cc(O)cc(O)c12]
X1 = R1
X2 = R2
X3 = R1
X4 = R1
X6 = R1
Y2 = R1
Y3 = R1
Y4 = R1
Y5 = R1
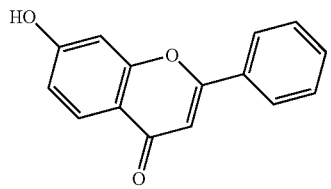 [SMILES: O=c1cc(-c2ccccc2)oc2cc(O)ccc12]
X1 = R1
X2 = R2
X3 = R2
X4 = R2
X6 = R1
Y2 = R1
Y3 = R1
Y4 = R1
Y5 = R1
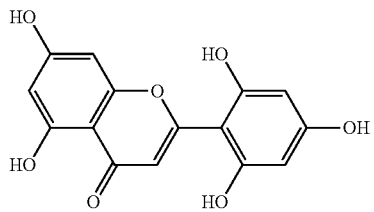 [SMILES: O=c1cc(-c2c(O)cc(O)cc2O)oc2cc(O)cc(O)c12]
X1 = R1
X2 = R2
X3 = R1
X4 = R1
X6 = R1
Y2 = R1
Y3 = R1
Y4 = R1
Y5 = R1
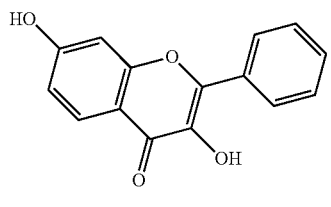 [SMILES: O=c1c(O)c(-c2ccccc2)oc2cc(O)ccc12]
X1 = R1
X2 = R2
X3 = R1
X4 = R1
X6 = R2
Y2 = R1
Y3 = R1
Y4 = R1
Y5 = R1

TABLE 7-continued

Compound Group II: Exemplary Derivatives of N4A and YN1

X1 = R1
X2 = R2
X3 = R1
X4 = R1
X6 = R1
Y2 = R1
Y3 = R1
Y4 = R1
Y5 = R1

X1 = R1
X2 = R2
X3 = R1
X4 = R1
X6 = R1
Y2 = R1
Y3 = R1
Y4 = R1
Y5 = R1

TABLE 8

Compound Group III (RBC2 Group): Template and Exemplary R groups

| Template | Representative Compound Tested |
| --- | --- |
| X1 = R1, R4, or R5<br>X2 = R1 or R3<br>X3 = R1 or R2<br>X4 = R1 or R2 | (Z)-ethyl-3-((1,4-dihydroxynaphthalen-2-yl)thio)but-2-enoate<br>RBC2, NSC278631 |

R groups

R1 —H

R2 —OH

R3

R4

R5

TABLE 9

Compound Group III: Exemplary Derivatives of RBC2

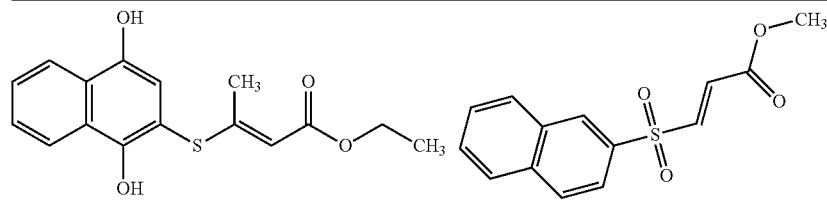

X1 = R1
X2 = R3
X3 = R2
X4 = R2

X1 = R4
X2 = R1
X3 = R1
X4 = R1

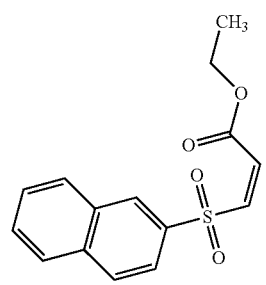 [SMILES: CCOC(=O)/C=C\S(=O)(=O)c1ccc2ccccc2c1]

X1 = R5
X2 = R1
X3 = R1
X4 = R1

Example 7

Future Evaluation of Antiproliferative and Antimetastatic Activities of PFKFB3 Inhibitors in BALB/c Athymic Nude Mice We have demonstrated that the PFKFB3 inhibitors significantly inhibit the growth and viability of human breast cancer and cervical cancer cells in vitro. The MDA-MB-231 breast cancer cell line is known to be highly malignant, to be estrogen-independent, and to display anchorage-independent growth when cultured in soft agarose gels. When MDA-MB-231 cells are injected subcutaneously into the flanks of female BALB/c athymic nude mice, they form rapidly-growing, anaplastic adenocarcinomas that are highly invasive, and that typically metastasize into the lungs and bones. The most active PFKFB3 inhibitors analogues from the in vitro assays will be examined for their antiproliferative and anti-invasive activity in vivo. MDA-MB-231 cells transfected with green fluorescence protein (GFP) gene will be grown in culture, isolated with 0.25% trypsin and 0.53 mM EDTA solution, washed, counted and diluted to a desired concentration in fresh, complete growth culture medium. Briefly, 1×106 MDA-MB-231-GFP cells in 100 μL of serum-free RPMI 1640 are injected subcutaneously into the flanks of nude mice using a 1-mL syringe with a 26-gauge, sterile needle. All surgical operations will be performed under aseptic conditions. Nude mice with similar tumor sizes, about 100 mm3 (2 weeks post-inoculation) will be selected and randomly divided into five groups (n=9 per group): control (DMSO vehicle); one group for each of currently identified PFKFB3 inhibitors. Animal weights and tumor growth and metastases will be monitored weekly. Average tumor diameter for each palpable tumor will be determined as the mean of the two largest perpendicular diameters, measured by vernier calipers. Four to six weeks after tumor cell implantation, tumors in all mice are expected to reach approximately 1 cm in diameter. Detection and quantification of primary and metastatic tumors in anesthetized animals in each treatment group will be performed with a known imaging system, for example, the Kodak In-Vivo Imaging System FX Pro Imaging System. Animals will then be given intraperitoneal injections daily for one week, either with vehicle (DMSO) or with the test compound. A dose of the test compound will be used based on the cell experiments and $GI_{50}$ values. If the dose should be too toxic, an alternative effective dose (middle dose) can be estimated by extrapolation from results obtained from the in vitro studies. A lower dose (½ middle dose) and a high dose (2× middle dose) can then be tested. The doses for each compound can also be titrated to the maximum tolerated doses that do not produce apparent toxicity.)

Afterwards, primary and metastatic tumors in each animal will be re-scanned with the same imaging system to determine treatment effects on primary and metastatic tumor growth. Animals will be examined every three days for evidence of tumors by fluoroimaging, and the rate of tumor growth monitored by estimating tumor volume. Animals will be examined for secondary tumors in multiple organs by observing the presence of fluorescent cell colonies. At the end of the experimental period, animals will be sacrificed. Tumors will be excised, weighed, and prepared for later histological examination. Wet sections of organs will be examined for the presence of green fluorescent protein. Other tissue portions will be fixed in neutral buffered formalin and embedded in paraffin. 5.0 μm-thick sections (or appropriate section thickness) of tumors will be processed for H&E staining. Testing activity against established tumors provides a different (and generally more stringent) test of in vivo anti-tumor activity than the ability to inhibit the formation of new tumors. Results from these experiments are expected to confirm that PFKFB3 inhibitors can prevent or significantly delay tumor formation and metastasis in vivo. All animal experiments will be approved by the applicable Institutional Animal Care and Use Committee. All surgical and treatment procedures will be consistent with the IACUC policies and procedures, and applicable laws and regulations. Following successful animal testing, clinical trials in humans will be conducted in accordance with applicable laws and regulations.

Statistical Analysis. All experimental treatments will be run at least in triplicate. One-way ANOVA is used to evaluate results statistically. Significance is determined by the Newman-Keuls test. Differences are considered statistically significant at p<0.05.

Compounds used in the present invention may be administered to a patient by any suitable means, including intravenous, parenteral, subcutaneous, intrapulmonary, and intranasal administration. Parenteral infusions include intramuscular, intravenous, intraarterial, or intraperitoneal administration. The compounds may also be administered transdermally, for example in the form of a slow-release subcutaneous implant. They may also be administered by inhalation.

Pharmaceutically acceptable carrier preparations include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampoule, each containing a unit dose amount, or in the form of a container containing multiple doses.

A method for controlling the duration of action comprises incorporating the active compound into particles of a polymeric substance such as a polyester, peptide, hydrogel, polylactide/glycolide copolymer, or ethylenevinylacetate copolymers. Alternatively, an active compound may be encapsulated in nanoparticles or microcapsules by techniques otherwise known in the art including, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

As used herein, an "effective amount" of a compound is an amount, that when administered to a patient (whether as a single dose or as a time course of treatment) inhibits or reduces the growth of targeted tumors to a clinically significant degree; or alternatively, to a statistically significant degree as compared to control. "Statistical significance" means significance at the P<0.05 level, or such other measure of statistical significance as would be used by those of skill in the art of biomedical statistics in the context of a particular type of treatment.

The complete disclosures of all references cited in this specification are hereby incorporated by reference. Also incorporated by reference is the complete disclosure of the priority application, provisional patent application Ser. No. 61/484,386; as well as the complete disclosures of all references cited in the priority application. In the event of an otherwise irreconcilable conflict, however, the present specification shall control.

REFERENCES

[1] Sousa, S. F., et al., Virtual screening in drug design and development. Combinatorial Chemistry & High Throughput Screening, 2010. 13(5): p. 442-53.
[2] Tuccinardi, T., Docking-Based Virtual Screening: Recent Developments. Combinatorial Chemistry & High Throughput Screening, 2009. 12(3): p. 303-314.
[3] Villoutreix, B. O., R. Eudes, and M. A. Miteva, Structure-Based Virtual Ligand Screening: Recent Success Stories. Combinatorial Chemistry & High Throughput Screening, 2009. 12(10): p. 1000-1016.
[4] Parker, C. N. and J. Bajorath, Towards unified compound screening strategies: A critical evaluation of error sources in experimental and virtual high-throughput screening. Qsar & Combinatorial Science, 2006. 25(12): p. 1153-1161.
[5] Klebe, G, Virtual ligand screening: strategies, perspectives and limitations. Drug Discovery Today, 2006. 11(13-14): p. 580-594.
[6] Guido, R. V., G Oliva, and A. D. Andricopulo, Virtual Screening and Its Integration with Modern Drug Design Technologies. Current Medicinal Chemistry, 2008. 15(1): p. 37-46.
[7] Maiorov, V. and R. P. Sheridan, Enhanced virtual screening by combined use of two docking methods: getting the most on a limited budget. J. Chem. Inf. Model., 2005. 45(4): p. 1017-23.
[8] van Montfort, R. L. and P. Workman, Structure-based design of molecular cancer therapeutics. Trends in Biotechnology, 2009. 27(5): p. 315-328.
[9] Nagarajan, S., et al., IKK beta inhibitors identification part II: Ligand and structure-based virtual screening. Bioorganic & Medicinal Chemistry, 2010. 18(11): p. 3951-3960.
[10] Lee, K., et al., Pharmacophore modeling and virtual screening studies for new VEGFR-2 kinase inhibitors. European Journal of Medicinal Chemistry, 2010. 45(11): p. 5420-5427.
[11] Marsden, B. D. and S. Knapp, Doing more than just the structure-structural genomics in kinase drug discovery. Curr Opin Chem Biol, 2008. 12(1): p. 40-5.
[12] Chesney, J., 6-phosphofructo-2-kinase/fructose-2,6-bisphosphatase and tumor cell glycolysis. Curr. Opin. Clin. Nutr. Metab. Care., 2006. 9(5): p. 535-9.
[13] Pilkis, S. J., et al., 6-Phosphofructo-2-kinase/fructose-2,6-bisphosphatase: a metabolic signaling enzyme. Annu. Rev. Biochem., 1995. 64: p. 799-835.

[14] Rider, M. H., et al., 6-phosphofructo-2-kinase/fructose-2,6-bisphosphatase: head-to-head with a bifunctional enzyme that controls glycolysis. Biochem. J., 2004. 381: p. 561-579.

[15] Yalcin, A., et al., Regulation of glucose metabolism by 6-phosphofructo-2-kinase/fructose-2,6-bisphosphatases in cancer. Exp. Mol. Pathol., 2009. 86(3): p. 174-9.

[16] Kim, J. W. and C. V. Dang, Cancer's molecular sweet tooth and the Warburg effect. Cancer Research, 2006. 66: p. 8927-8930.

[17] Hsu, P. P. and D. M. Sabatini, Cancer cell metabolism: Warburg and beyond. Cell, 2008. 134(5): p. 703-7.

[18] Kroemer, G and J. Pouyssegur, Tumor cell metabolism: cancer's Achilles' heel. Cancer Cell, 2008. 13: p. 472-482.

[19] Atsumi, T., et al., High expression of inducible 6-phosphofructo-2-kinase/fructose-2,6-bisphosphatase (iPFK-2; PFKFB3) in human cancers. Cancer Research, 2002. 62(20): p. 5881-7.

[20] Kim, S. G, et al., Crystal structure of the hypoxia-inducible form of 6-phosphofructo-2-kinase/fructose-2,6-bisphosphatase (PFKFB3): a possible new target for cancer therapy. J. Biol. Chem., 2006. 281: p. 2939-2944.

[21] Van Schaftingen, E., et al., A kinetic study of pyrophosphate: fructose-6-phosphate phosphotransferase from potato tubers. Application to a microassay of fructose 2,6-bisphosphate. Eur. J. Biochem., 1982. 129(1): p. 191-5.

[22] Ewing, T. J., et al., DOCK 4.0: search strategies for automated molecular docking of flexible molecule databases. Journal of Computer-Aided Molecular Design, 2001. 15(5): p. 411-28.

[23] Rarey, M., et al., A fast flexible docking method using an incremental construction algorithm. Journal of molecular biology, 1996. 261(3): p. 470-89.

[24] Jones, G., et al., Development and validation of a genetic algorithm for flexible docking. Journal of molecular biology, 1997. 267(3): p. 727-48.

[25] MOE (Molecular Operating Environment) 2010, Chemical Computing Group: Montreal, Canada.

[26] Trott, O. and A. J. Olson, AutoDock Vina: improving the speed and accuracy of docking with a new scoring function, efficient optimization, and multithreading. Journal of Computational Chemistry, 2010. 31(2): p. 455-61.

[27] Kim, S.-G, et al., A direct substrate-substrate interaction found in the kinase domain of the bifunctional enzyme, 6-phosphofructo-2-kinase/fructose-2,6-bisphosphatase. J. Mol. Biol., 2007. 370: p. 14-26.

[28] Plewczynski, D., et al., Can We Trust Docking Results? Evaluation of Seven Commonly Used Programs on PDBbind Database. Journal of Computational Chemistry, 2011. 32(4): p. 742-755.

[29] Li, X., et al., Evaluation of the Performance of Four Molecular Docking Programs on a Diverse Set of Protein-Ligand Complexes. Journal of Computational Chemistry, 2010. 31(11): p. 2109-2125.

[30] Kruger, D. M. and A. Evers, Comparison of Structure- and Ligand-Based Virtual Screening Protocols Considering Hit List Complementarity and Enrichment Factors. Chemmedchem, 2010. 5(1): p. 148-158.

[31] Tan, L., et al., Integrating structure- and ligand-based virtual screening: comparison of individual, parallel, and fused molecular docking and similarity search calculations on multiple targets. Chemmedchem, 2008. 3(10): p. 1566-71.

[32] Swann, S. L., et al., A unified, probabilistic framework for structure- and ligand-based virtual screening. Journal of medicinal chemistry, 2011. 54(5): p. 1223-32.

[33] GraphPad, GraphPad Prism 5, 2011, GraphPad Software.

[34] Jones R G, Thompson C B (2009) Tumor suppressors and cell metabolism: a recipe for cancer growth. Genes Dev 23: 537-548.

[35] Warburg 0 (1956) On the origin of cancer cells. Science 123: 309-314.

[36] Vander Heiden M G Cantley L C, Thompson C B (2009) Understanding the Warburg effect: the metabolic requirements of cell proliferation. Science 324: 1029-1033.

[37] Garber K (2006) Energy deregulation: licensing tumors to grow. Science 312: 1158-1159.

[38] Hsu P P, Sabatini D M (2008) Cancer cell metabolism: Warburg and beyond. Cell 134: 703-707.

[39] Polyak K, Li Y, Zhu H, Lengauer C, Willson J K, et al. (1998) Somatic mutations of the mitochondrial genome in human colorectal tumours. Nat Genet. 20: 291-293.

[40] Gottlieb E, Tomlinson I P (2005) Mitochondrial tumour suppressors: a genetic and biochemical update. Nat Rev Cancer 5: 857-866.

[41] Pouyssegur J, Dayan F, Mazure N M (2006) Hypoxia signalling in cancer and approaches to enforce tumour regression. Nature 441: 437-443.

[42] DeBerardinis R J, Lum J J, Hatzivassiliou G, Thompson C B (2008) The biology of cancer: metabolic reprogramming fuels cell growth and proliferation. Cell Metab 7: 11-20.

[43] Pelicano H, Martin D S, Xu R H, Huang P (2006) Glycolysis inhibition for anticancer treatment. Oncogene 25: 4633-4646.

[44] Xu R H, Pelicano H, Zhou Y, Carew J S, Feng L, et al. (2005) Inhibition of glycolysis in cancer cells: a novel strategy to overcome drug resistance associated with mitochondrial respiratory defect and hypoxia. Cancer Res 65: 613-621.

[45] Tennant D A, Duran R V, Gottlieb E (2010) Targeting metabolic transformation for cancer therapy. Nat Rev Cancer 10: 267-277.

[46] Pilkis S J, Claus T H, Kurland I J, Lange A J (1995) 6-Phosphofructo-2-kinase/fructose-2,6-bisphosphatase: a metabolic signaling enzyme. Annu Rev Biochem 64: 799-835.

[47] El-Maghrabi M R, Noto F, Wu N, Manes N (2001) 6-phosphofructo-2-kinase/fructose-2,6-bisphosphatase: suiting structure to need, in a family of tissue-specific enzymes. Curr Opin Clin Nutr Metab Care 4: 411-418.

[48] Van Schaftingen E, Jett M F, Hue L, Hers H G (1981) Control of liver 6-phosphofructokinase by fructose 2,6-bisphosphate and other effectors. Proc Natl Acad Sci USA 78: 3483-3486.

[49] Nissler K, Petermann H, Wenz I, Brox D (1995) Fructose 2,6-bisphosphate metabolism in Ehrlich ascites tumour cells. J Cancer Res Clin Oncol 121: 739-745.

[50] Hue L, Rousseau G G (1993) Fructose 2,6-bisphosphate and the control of glycolysis by growth factors, tumor promoters and oncogenes. Adv Enzyme Regul 33: 97-110.

[51] Telang S, Yalcin A, Clem A L, Bucala R, Lane A N, et al. (2006) Ras transformation requires metabolic control by 6-phosphofructo-2-kinase. Oncogene 25: 7225-7234.

[52] Rider M H, Bertrand L, Vertommen D, Michels P A, Rousseau G G, et al. (2004) 6-phosphofructo-2-kinase/ fructose-2,6-bisphosphatase: head-to-head with a bifunctional enzyme that controls glycolysis. Biochem J 381: 561-579.

[53] Minchenko O, Opentanova I, Caro J (2003) Hypoxic regulation of the 6-phosphofructo-2-kinase/fructose-2,6-bisphosphatase gene family (PFKFB-1-4) expression in vivo. FEBS Lett 554: 264-270.

[54] Atsumi T, Chesney J, Metz C, Leng L, Donnelly S, et al. (2002) High expression of inducible 6-phosphofructo-2-kinase/fructose-2,6-bisphosphatase (iPFK-2; PFKFB3) in human cancers. Cancer Res 62: 5881-5887.

[55] Calvo M N, Bartrons R, Castano E, Perales J C, Navarro-Sabate A, et al. (2006) PFKFB3 gene silencing decreases glycolysis, induces cell-cycle delay and inhibits anchorage-independent growth in HeLa cells. FEBS Lett 580: 3308-3314.

[56] Minchenko A, Leshchinsky I, Opentanova I, Sang N, Srinivas V, et al. (2002) Hypoxia-inducible factor-1-mediated expression of the 6-phosphofructo-2-kinase/fructose-2,6-bisphosphatase-3 (PFKFB3) gene. Its possible role in the Warburg effect. J Biol Chem 277: 6183-6187.

[57] Clem B, Telang S, Clem A, Yalcin A, Meier J, et al. (2008) Small-molecule inhibition of 6-phosphofructo-2-kinase activity suppresses glycolytic flux and tumor growth. Mol Cancer Ther 7: 110-120.

[58] Kim S G Manes N P, El-Maghrabi M R, Lee Y H (2006) Crystal structure of the hypoxia-inducible form of 6-phosphofructo-2-kinase/fructose-2,6-bisphosphatase (PFKFB3): a possible new target for cancer therapy. J Biol Chem 281: 2939-2944.

[59] Gohlke H, Hendlich M, Klebe G (2000) Knowledge-based scoring function to predict protein-ligand interactions. J Mol Biol 295: 337-356.

[60] McConkey D J (1998) Biochemical determinants of apoptosis and necrosis. Toxicol Lett 99: 157-168.

[61] Richter C, Schweizer M, Cossarizza A, Franceschi C (1996) Control of apoptosis by the cellular ATP level. FEBS Lett 378: 107-110.

[62] Kim S G Cavalier M, El-Maghrabi M R, Lee Y H (2007) A direct substrate-substrate interaction found in the kinase domain of the bifunctional enzyme, 6-phosphofructo-2-kinase/fructose-2,6-bisphosphatase. J Mol Biol 370: 14-26.

[63] Perez J J (2005) Managing molecular diversity. Chem Soc Rev 34: 143-152.

[64] Beene D L, Brandt G S, Zhong W, Zacharias N M, Lester H A, et al. (2002) Cation-pi interactions in ligand recognition by serotonergic (5-HT3A) and nicotinic acetylcholine receptors: the anomalous binding properties of nicotine. Biochemistry 41: 10262-10269.

[65] Kuntz I D (1992) Structure-based strategies for drug design and discovery. Science 257: 1078-1082.

[66] Blundell T L, Jhoti H, Abell C (2002) High-throughput crystallography for lead discovery in drug design. Nat Rev Drug Discov 1: 45-54.

[67] Davies S P, Reddy H, Caivano M, Cohen P (2000) Specificity and mechanism of action of some commonly used protein kinase inhibitors. Biochem J 351: 95-105.

[68] Hanks S K, Quinn A M, Hunter T (1988) The protein kinase family: conserved features and deduced phylogeny of the catalytic domains. Science 241: 42-52.

[69] Van Schaftingen E, Lederer B, Bartrons R, Hers H G (1982) A kinetic study of pyrophosphate: fructose-6-phosphate phosphotransferase from potato tubers. Application to a microassay of fructose 2,6-bisphosphate. Eur J Biochem 129: 191-195.

[70] Cleland W W (1979) Statistical analysis of enzyme kinetic data. Methods Enzymol 63: 103-138.

[71] van Engeland M, Nieland L J, Ramaekers F C, Schutte B, Reutelingsperger C P (1998) Annexin V-affinity assay: a review on an apoptosis detection system based on phosphatidylserine exposure. Cytometry 31: 1-9.

[72] Kabsch W (2010) Xds. Acta Crystallogr D Biol Crystallogr 66: 125-132.

[73] (1994) The CCP4 suite: programs for protein crystallography. Acta Crystallogr D Biol Crystallogr 50: 760-763.

What is claimed:

1. A method of inhibiting an isozyme of 6-phosphofructo-2-kinase/fructose-2,6-bisphosphatase (PFKFB) in a mammal; wherein the mammal has a cancer in which a PFKFB isozyme is overexpressed; said method comprising administering to the mammal an effective amount of a compound having the formula:

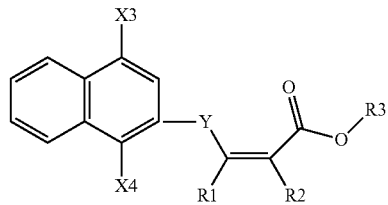

wherein:
X3 is —OH, and X4 is —OH;
Y is —S— or

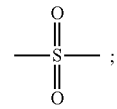

R1 and R2 are independently selected from the group consisting of —H, and —CH$_3$; and R1 and R2 may be the same or different;
R3 is —CH$_3$ or —CH$_2$CH$_3$; and
the configuration at the carbon-carbon double bond that is depicted in the formula between R1 and R2 is either E or Z.

2. The method of claim 1 wherein the isozyme of PFKFB is PFKFB3.

3. The method of claim 2 wherein PFKFB3 is preferentially inhibited relative to at least one other PFKFB isozyme.

4. The method of claim 1, wherein the compound is (Z)-ethyl 3-((1,4-dihydroxynaphthalen-2-yl)thio)but-2-enoate.

5. The method of claim 1, wherein the overexpressed isozyme is PFKFB3.

* * * * *